(12) United States Patent
Hahn et al.

(10) Patent No.: US 12,121,536 B2
(45) Date of Patent: *Oct. 22, 2024

(54) STRONTIUM BASED COMPOSITIONS AND FORMULATIONS FOR PAIN, PRURITUS, AND INFLAMMATION

(71) Applicant: Galleon Labs LLC, Naples, FL (US)

(72) Inventors: Gary S. Hahn, San Diego, CA (US); Siva Gudi, San Diego, CA (US)

(73) Assignee: Galleon Labs LLC, Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/646,805

(22) Filed: Jan. 3, 2022

(65) Prior Publication Data

US 2022/0323485 A1 Oct. 13, 2022

Related U.S. Application Data

(63) Continuation of application No. 16/412,286, filed on May 14, 2019, now Pat. No. 11,235,002, which is a continuation of application No. 15/437,684, filed on Feb. 21, 2017, now abandoned, which is a continuation-in-part of application No. 15/239,171, filed on Aug. 17, 2016, now abandoned.

(60) Provisional application No. 62/208,249, filed on Aug. 21, 2015.

(51) Int. Cl.
| | |
|---|---|
| *A61K 33/00* | (2006.01) |
| *A61K 9/00* | (2006.01) |
| *A61K 31/19* | (2006.01) |
| *A61K 31/198* | (2006.01) |
| *A61K 31/22* | (2006.01) |
| *A61K 33/14* | (2006.01) |
| *A61K 47/32* | (2006.01) |
| *A61K 47/54* | (2017.01) |
| *A61K 31/455* | (2006.01) |
| *A61K 33/18* | (2006.01) |
| *A61K 33/38* | (2006.01) |
| *A61K 45/06* | (2006.01) |

(52) U.S. Cl.
CPC ............ *A61K 33/00* (2013.01); *A61K 9/0014* (2013.01); *A61K 31/19* (2013.01); *A61K 31/198* (2013.01); *A61K 31/22* (2013.01); *A61K 33/14* (2013.01); *A61K 47/32* (2013.01); *A61K 47/542* (2017.08); *A61K 9/0053* (2013.01); *A61K 31/455* (2013.01); *A61K 33/18* (2013.01); *A61K 33/38* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,833,732 | A | 9/1974 | Saeed et al. |
| 4,477,439 | A | 10/1984 | D'Alelio |
| 5,716,625 | A | 2/1998 | Hahn et al. |
| 5,804,203 | A | 9/1998 | Hahn et al. |
| 5,824,650 | A | 10/1998 | De Lacharriere et al. |
| 5,851,556 | A | 12/1998 | Breton et al. |
| 5,866,168 | A | 2/1999 | De Lacharriere et al. |
| 6,051,609 | A | 4/2000 | Yu et al. |
| 6,623,730 | B1 | 9/2003 | Williams et al. |
| 7,404,967 | B2 | 7/2008 | Hahn et al. |
| 9,333,185 | B2 | 5/2016 | Hahn |
| 9,480,704 | B2 | 11/2016 | Hahn |
| 10,159,693 | B2 | 12/2018 | Hahn |
| 10,874,689 | B2 | 12/2020 | Hahn |
| 11,235,002 | B2 | 2/2022 | Hahn et al. |
| 2003/0198656 | A1 | 10/2003 | Yu et al. |
| 2004/0248942 | A1 | 12/2004 | Hepburn et al. |
| 2006/0111307 | A1 | 5/2006 | Robbins |
| 2006/0236470 | A1 | 10/2006 | Sabnis et al. |
| 2007/0134232 | A1 | 6/2007 | Studin et al. |
| 2008/0096872 | A1 | 4/2008 | Friedman |
| 2009/0087401 | A1 | 4/2009 | Hiramoto et al. |
| 2009/0131364 | A1 | 5/2009 | Dharmesh et al. |
| 2009/0214628 | A1 | 8/2009 | de Rijk |
| 2010/0099640 | A1 | 4/2010 | Geuns et al. |
| 2010/0173021 | A1 | 7/2010 | Hahn et al. |
| 2010/0226987 | A1 | 9/2010 | Gnaim et al. |
| 2010/0247461 | A1 | 9/2010 | Voronkov et al. |
| 2011/0129433 | A1 | 6/2011 | Currie et al. |
| 2012/0255574 | A1 | 10/2012 | Flohr et al. |

(Continued)

FOREIGN PATENT DOCUMENTS

| | | |
|---|---|---|
| EP | 0219455 A2 | 4/1987 |
| EP | 0273202 A2 | 7/1988 |

(Continued)

OTHER PUBLICATIONS

Ahern, et al., "Extracellular Cations Sensitize and Gate Capsaicin Receptor TRPV1 Modulating Pain Signaling", J Neuroscience, May 25, 2005; 25(21):5109-5116.
Cabrera, et al., "Beneficial Effects of Green Tea—A Review." J Am College of Nutrition, Apr. 30, 2006, 25(2):79-99.

(Continued)

*Primary Examiner* — Bethany P Barham
*Assistant Examiner* — Barbara S Frazier
(74) *Attorney, Agent, or Firm* — Knobbe, Martens, Olson & Bear, LLP

(57) ABSTRACT

Therapeutically-active compositions and formulations for treating pain, pruritus, irritation, inflammation, and tissue damage due to the irritation and inflammation, and therapeutically-active compositions and formulations for wound management, including wounds that are at high risk for infection. Strontium and beta hydroxybutyrate based compositions and formulations which can be topically applied.

20 Claims, No Drawings

(56) References Cited

U.S. PATENT DOCUMENTS

| | | |
|---|---|---|
| 2012/0328593 A1 | 12/2012 | Huang et al. |
| 2013/0130959 A1 | 5/2013 | Li et al. |
| 2016/0250253 A1 | 9/2016 | Hahn |
| 2016/0361357 A1 | 12/2016 | Hahn |
| 2017/0049807 A1 | 2/2017 | Hahn |
| 2017/0157169 A1 | 6/2017 | Hahn et al. |
| 2021/0177888 A1 | 6/2021 | Hahn et al. |

FOREIGN PATENT DOCUMENTS

| | | |
|---|---|---|
| EP | 0273202 B1 | 6/1995 |
| GB | 0487094 A | 6/1938 |
| JP | 2003-509366 A | 3/2003 |
| JP | 2004-167218 A | 6/2004 |
| JP | 2005-507396 | 3/2005 |
| JP | 2011-502505 A | 1/2011 |
| KR | 1019980700842 | 4/1998 |
| RU | 2124353 | 1/1999 |
| WO | WO 2003/028742 | 4/2003 |
| WO | WO 2006/069293 | 6/2006 |
| WO | WO 2007/000779 | 10/2007 |
| WO | WO 2013/142383 A1 | 9/2013 |
| WO | WO 2016/141219 A1 | 9/2016 |

OTHER PUBLICATIONS

Cao, et al., "Intracellular Proton-mediated Activation of TRPV3 Channels Accounts for the Exfoliation Effect of a-Hydroxyl Acids on Keratinocytes", J Biol Chem. (2012), 287(31):25905-25916.

Chen, et al., "Acid mediates a prolonged antinociception via substance P signaling in acid-induced chronic widespread pain" Molecular Pain 2014, 10:30 in 5 pages.

Chen, et al., "Expression and function of proton-sensing G-protein-coupled receptors in inflammatory pain" Molecular Pain 2009, 5:39 in 19 pages.

Chen, et al., "Roles of ASIC3, TRPV1, and NaV1.8 in the transition from acute to chronic pain in a mouse model of fibromyalgia" Molecular Pain 2014, 10:40 in 15 pages.

Dai, et al., "Plant Phenolics: Extraction, Analysis and Their Antioxidant and Anticancer Properties." Molecules, Oct. 21, 2010, 15:7313-7352.

Du, et al., "Modulation of TRPM2 by acidic pH and the underlying mechanisms for pH sensitivity", J Gen Physiol. 2009, 134(6):471-488.

Frey-Law, et al., "Acidic Buffer Induced Muscle Pain Evokes Referred Pain and Mechanical Hyperalgesia in Humans", Pain. 2008; 140(2):254-264.

Gamper, et al., "Redox and Nitric Oxide-Mediated Regulation of Sensory Neuron Ion Channel Function", Antioxid. Redox Signal. 2015, 22(6):486-504.

Gregory, et al., "Effect of Intramuscular Protons, Lactate, and ATP on Muscle Hyperalgesia in Rats" PLOS One, 2015, 10(9):e138576 in 13 pages.

Hahn, "Strontium is a Potent and Selective Inhibitor of Sensory Irritation" Dermatologic Surgery 25:689-694, 1999.

Hansen, et al., "Modulation of the Dimer Interface at Ionotropic Glutamate-Like Receptor 2 by D-Serine and Extracellular Calcium" The Journal of Neuroscience, Jan. 28, 2009 • 29(4) pp. 907-917.

Hasegawa, et al., "Cysteine, Histidine and Glycine Exhibit Anti-Inflammatory Effects in Human Coronary Arterial Endothelial Cells", Clin Exper Immunol. 2012, 167(2):269-274.

Huang, et al., "Acidosis Mediates the Switching of Gs-PKA and Gi-PKCε Dependence in Prolonged Hyperalgesia Induced by Inflammation" PLo One, 2015, 10(5):e0125022 in 17 pages.

Iacob, et al., "Gene expression factor analysis to differentiate pathways linked to fibromyalgia, chronic fatigue syndrome, and depression in a diverse patient sample", Arthritis Care Res. 2015, 68(1):132-140.

Jara-Oseguera et al. "TRPV1: On the Road to Pain Relief" Curr Mol Pharmacol. Nov. 2008 ; 1(3): 255-269.

Joksovic et al., "CaV3.2 is the major molecular substrate for redox regulation of T-type Ca2+ channels in the rat and mouse thalamus", J Physiol. (2006) 574(2):415-430.

Jones, "Physicochemical Properties of Pharmaceutical Polymers", in Pharmaceutical Applications of Polymers for Drug Delivery, Smithers Rapra Publishing, Jan. 1, 2004, pp. 3-13.

Katiyar et al., "Green Tea Polyphenolic Antioxidants and Skin photoprotection." Int J Oncol., 2001, 18(6):1307-1313.

Kim et al., "Gallic Acid Inhibits Histamine Release and Pro-Inflammatory Cytokine Production in Mast Cells" Toxicological Sciences 91(1):123-131, 2006.

Lee, et al., "The calcium-sensing receptor regulates the NLRP3 inflammasome through Ca2+ and cAMP" Nature. Dec. 6, 2012; 492(7427): 123-127.

Madlener, et al., "Gallic acid inhibits ribonucleotide reductase and cyclooxygenases in human HL-60 promyelocytic leukemia cells" Cancer Letters, 245:156-162, 2007.

Meyers, et al., "The Effect of Selected Amino Acids on Gelatin-Induced Inflammation in Adult Male Mice." Inflammation, 1979, 3(3):225-233.

Morales-Lazaro, et al., "The role of endogenous molecules in modulating pain through transient receptor potential vanilloid 1 (TRPV1)", J Physiol. 2013, 591(13):3109-3121.

Nelson, et al., "The Endogenous Redox Agent L-Cysteine Induces T-Type Ca2+ Channel-Dependent Sensitization of a Novel Subpopulation of Rat Peripheral Nociceptors", J Neurosci., 2005, 25(38):8766-8775.

Nelson, et al., "Reducing Agents Sensitize C-Type Nociceptors by Relieving High-Affinity Zinc Inhibition of T-Type Calcium Channels", J Neurosci., 2007, 27(31):8250-8260.

Pae C-U., "The Potential Role of Monocyte Chemoattractant Protein-1 for Major Depressive Disorder" Psychiatry Investig. 2014; 11(3):217-222.

Pearson, The Biology Place, http://www.phschool.com/science/biology_place/bioprop/landd.html, accessed Jan. 1, 2016.

Pollak, et al., "Exogenously Applied Muscle Metabolites Synergistically Evoke Sensations of Muscle Fatigue and Pain in Human Subjects", Exp Physiol. 2014, 99(2):368-380.

Raison, et al., "Association of peripheral inflammatory markers with chronic fatigue in a population-based sample",Brain Behav Immun. 2009, 23(3):327-337.

Sansone et al., "Getting a Knack for NAC: N-Acetyl-Cysteine". Clin Neuroscience. 2011, 8(1): 10-14.

Senaldi, et al., "Protective Effect of N-Acetylcysteine in Hapten-Induced Irritant and Contact Hypersensitivity Reactions" The Journal of Investigative Dermatology, 102(6): 934-937, Jun. 1994.

Sluka, et al., "Chronic hyperalgesia induced by repeated acid injections in muscle is abolished by the loss of ASIC3, but not ASIC1", Pain. 2003, 106(3):229-239.

Sluka, et al., "The dichotomized role for acid sensing ion channels in musculoskeletal pain and inflammation", Neuropharmacol. 2015, 94:58-63.

Steen, et al., "A Dominant Role of Acid pH in Inflammatory Excitation and Sensitization of Nociceptors in Rat Skin, in vitro", J Neuroscience, 1995, 15(5):3982-3989.

Stone, et al., "Combined, but not individual, blockade of ASIC3, P2X, and EP4 receptors attenuates the exercise pressor reflex in rats with freely perfused hindlimb muscles", J Appl Physiol. (2015) 19:1330-1336.

Sugiura, et al., "Mouse colon sensory neurons detect extracellular acidosis via TRPV1", Am J Physiol Cell Physiol. 2007, 292:C1768-C1774.

Susankova, et al., "Reducing and Oxidizing Agents Sensitize Heat-Activated Vanilloid Receptor (TRPV1) Current", Mol Pharmacol. (2006), 70(1):383-394.

Todorovic, et al., "Redox Regulation of Neuronal Voltage-Gated Calcium Channels" Antioxid Redox Signal. (2014), 21(6):880-891.

Walters, "Nociceptors as chronic drivers of pain and hyperreflexia after spinal cord injury: an adaptive-maladaptive hyperfunctional state hypothesis", Frontiers in Physiology, 2012; 3:309 in 13 pages.

Wemmie, et al., "Acid-sensing ion channels in pain and disease", Nat Rev Neurosci. 2013, 14(7):461-471.

(56) References Cited

OTHER PUBLICATIONS

Yang, et al., "Lactate promotes plasticity gene expression by potentiating NMDA signaling in neurons", PNAS, 2014, 111(33):12228-12233.
Zhai, et al., "Strontium nitrate suppresses chemically-induced sensory irritation in humans" Contact Dermatitis 42:98-100, 2000.
Chinese Office Action dated Dec. 21, 2020 for Application No. 201710097305.2.
Extended European Search Report dated Oct. 17, 2017 for European Patent Application No. 17156555.9.
European Office Action dated Jan. 15, 2021 for European Patent Application No. 17156555.9.
Japanese Office Action dated Dec. 25, 2020 for Japanese Application No. 2017-26907.
Indian Examination Report dated Apr. 15, 2021 for India Application No. 201741005887.

STRONTIUM BASED COMPOSITIONS AND FORMULATIONS FOR PAIN, PRURITUS, AND INFLAMMATION

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/412,286, filed May 14, 2019, and continuation of U.S. application Ser. No. 15/437,684, filed Feb. 21, 2017, which is a continuation-in-part of U.S. Ser. No. 15/239,171, filed on Aug. 17, 2016, which claims the benefit of U.S. Ser. No. 62/208,249, filed on Aug. 21, 2015. Each of the aforementioned applications is incorporated by reference herein in its entirety, and each is hereby expressly made a part of this specification.

TECHNICAL FIELD

The disclosure herein relates to therapeutically-active compositions and formulations for treating pain, pruritus, irritation, inflammation, and tissue damage due to the irritation and inflammation. The disclosure herein also related to therapeutically-active compositions and formulations for wound managements, including wounds that are at high risk for infection. In one embodiment, the disclosure relates to strontium and beta hydroxybutyrate based compositions and formulations which can be topically applied. In another embodiment, the disclosure relates to strontium and iodine or strontium and silver based compositions and formulations which can be topically applied.

BACKGROUND

Topically-applied strontium, in divalent ionic form, has the ability to rapidly suppress acute sensory irritation (e.g., stinging, burning, pain and/or itching) and accompanying inflammation due to chemical irritants, electromagnetic radiation, "environmental irritants," allergies, and diseases. While not being bound or otherwise limited by any particular biochemical mechanism, it has been theorized that strontium's anti-irritant activity was due to the ability of strontium to selectively suppress activation of Type C Nociceptors (TCN), the only sensory nerves that produce and transmit stinging, burning, pain, and itching sensations and the neurogenic inflammatory response that can accompany TCN activation.

When compared to existing topical drugs able to suppress sensory irritation like lidocaine or NOVOCAIN®, the local anesthetic typically used by dentists during dental procedures, strontium has a unique property—it is highly selective for only the TCN and doesn't significantly affect the many other sensory nerves that provide normal tactile sensations and "cutaneous awareness." Since lidocaine and other topical local anesthetics lack this specificity for TCN, they can cause numbness and loss of function.

SUMMARY

The following simplified summary provides a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented below.

In one embodiment, the disclosure herein relates to compositions and formulations comprising a strontium-containing component and beta hydroxybutyrate. In another embodiment, the disclosure herein relates to compositions and formulations comprising a strontium-containing component and iodine. In another embodiment, the disclosure herein relates to compositions and formulations comprising a strontium-containing component and silver. For any of the strontium based compositions and formulations disclosed herein, the strontium-containing component can be strontium chloride, strontium sulfate, strontium carbonate, strontium nitrate, strontium hydroxide, strontium hydrosulfide, strontium oxide, strontium acetate, strontium glutamate, strontium aspartate, strontium malonate, strontium maleate, strontium citrate, strontium threonate, strontium lactate, strontium pyruvate, strontium ascorbate, strontium alpha-ketoglutarate or strontium succinate, strontium carbonate, strontium bicarbonate, strontium hydroxide, strontium phosphate, or strontium citrate.

In another embodiment, any of the above described compositions and formulations further include at least one polyhydroxyphenol. The polyhydroxyphenol can be gallic acid, caffeic acid, tannic acid, epicatechin, epigallocatechin gallate, epigallocatechin, epicatechin gallate, ellagic acid, myricetin, luteolin, naringen, genistein, apagenin, nordihydroguaiaretic acid, esters thereof, or a combination of two or more of these agents.

In another embodiment, any of the above described compositions and formulations further include at least one cysteine based antioxidant. The cysteine based antioxidant can be cysteine, cystine, acetylcysteine, diacetylcysteine, esters thereof, or a combination of two or more of these agents.

In another embodiment, any of the above described compositions and formulations further include at least one beneficial agent. The beneficial agent can be aluminum acetate, aspartame, colloidal oatmeal, a corticosteroid, coal tar, an antidepressant, an antihistamine, a plant extract, a local anesthetic, a vitamin, a ceramide, a moisturizer, a polymer or a combination of two or more of these agents. When the beneficial agent is a corticosteroid, it is often selected from alclometasone dipropionate, amcinonide, betamethasone dipropionate, clobetasol propionate, desonide, desoximetasone, diflorasone diacetate, fluocinolone acetonide, fluocinonide, flurandrenolide, fluticasone propionate, halcinonide, halobetasol propionate, halometasone, hydrocortisone, hydrocortisone butyrate, hydrocortisone valerate, mometasone furoate, prednisone, triamcinolone acetonide, or a combination of two or more of these agents.

When the beneficial agent is an antidepressant, then it is often selected from amitriptyline, paroxetine, doxepin, hydroxyzine, mirtazapine, or a combination of two or more of these agents. When the beneficial agent is an antihistamine, it is often selected from acrivastine, azelastine, bilastine, brompheniramine, buclizine, bromodiphenhydramine, carbinoxamine, cetirizine, chlorpromazine, cyclizine, chlorpheniramine, chlorodiphenhydramine, clemastine, cyproheptadine, desloratadine, dexbrompheniramine, dexchlorpheniramine, dimenhydrinate, dimetindene, diphenhydramine, doxylamine, ebastine, embramine, fexofenadine, hydroxyzine, levocetirizine, loratadine, meclozine, mirtazapine, olopatadine, orphenadrine, phenindamine, pheniramine, phenyltoloxamine, promethazine, pyrilamine, quetiapine, rupatadine, tripelennamine, triprolidine, or a combination of two or more of these agents. When the beneficial agent is a plant extract, it is often selected from jewelweed, black current seed oil, ginger, tea tree oil, mint, thyme, menthol, camphor, chamomile, comfrey (allotonin), lavender, aloe, feverfew, soy, red hogweed (*Boerhavia diffusa*), marigold (*Calendula officinalis*), licorice, white willow bark, honey, green tea, frankincense, witch hazel, cloves, *Arnica montana*, basil, or a combination of two or more of these agents. When the beneficial agent is a local anesthetic, it is often selected from benzocaine, butamben, dibucaine, lidocaine, oxybuprocaine, pramoxine, proparacaine, proxymetacaine, or tetracaine, or a combination of two or more of these agents.

When the beneficial agent is a vitamin, it is often selected from vitamin B, vitamin B3 (niacin) vitamin C, vitamin D, vitamin E, vitamin K, tocopherol, ascorbic acid, or a combination of two or more of these agents. When the beneficial agent is a moisturizer, it is often selected from lipids, fats, oils, waxes, shea butter, lanolin, humectants, glycerol, honey, hyaluronic acid, silicone-based, allantoin, dimethicone, or ceramides, or a combination of two or more of these agents. When the beneficial agent is a polymer, it is often selected from polyvinylpyrrolidone (PVP), polyethylene glycol (PEG), cyclodextrins, carragenans, iota carrageenan, alginic acid, xanthan gum, guar gum, sulfated polysaccharides such as carrageenan, dextran sulfate, pentosan polysulfate, chondroitin sulfate, heparin sulfate, or a combination of two or more of these agent.

In another embodiment, the beneficial agent is corticosteroid. In another embodiment, the beneficial agent is an antidepressant. In another embodiment, the beneficial agent is an antihistamine. In another embodiment, the beneficial agent is a plant extract. In another embodiment, the beneficial agent is a local anesthetic. In another embodiment, the beneficial agent is a vitamin. In another embodiment, the beneficial agent is a moisturizer. In one embodiment, the beneficial agent is aspartame. In another embodiment, the beneficial agent is colloidal oatmeal. In another embodiment, beneficial agent is coal tar. In another embodiment, the beneficial agent is ceramide. In another embodiment, the beneficial agent is aluminum acetate. In another embodiment, the beneficial agent is hyaluronic acid. In another embodiment, the beneficial agent is dimethicone. In another embodiment, the beneficial agent is a polymer.

In another embodiment, the beneficial agent is a combination of at least two of the above mentioned beneficial agents. In another embodiment, the beneficial agent is a combination of at least three of the above mentioned beneficial agents. In another embodiment, the beneficial agent is a combination of at least four of the above mentioned beneficial agents.

In another embodiment, the composition or formulation comprises a strontium-containing component, beta hydroxybutyrate and acetylcysteine in a pharmaceutical carrier. In another embodiment, the composition or formulation comprises a strontium-containing component, beta hydroxybutyrate, and iodine in a pharmaceutical carrier. In another embodiment, the composition or formulation comprises a strontium-containing component, beta hydroxybutyrate, and silver in a pharmaceutical carrier.

In another embodiment, the above described compositions and formulations further include a skin penetration enhancer. Frequently the skin penetration enhancer is a sulfoxide, a dimethylsulfoxide, an azone, an azone derivatives, a pyrrolidone, a fatty acid, an essential oil, a terpene, a terpenoids, an oxazolidinone, a urea, a urea derivative, an alcohol, a glycol, an enzyme, a surfactant, a monoolein, an iminosulfuranes, or a phospholipid.

In another embodiment, the above described compositions and formulations further include an excipient such as those used to increase stability, increase disintegration of solid tablets, or increase customer appeal. Frequently the excipient is a preservative, a binder, a bulking agent, a diluent, a sweetener, a fragrance, a flavorant, a lubricant, or a colorant.

In another embodiment, the above described compositions and formulations are designed to be topically applied to epithelial tissue such as skin or mucous membranes. In another embodiment, the above described compositions and formulations can be designed to have a pH that is less than 5. Alternatively, the pH can be less than 4. Alternatively, the pH can be less than 3. In certain embodiments, the above described compositions and formulations are designed to have an osmolarity that is over 300 mOsm. Alternatively, the osmolarity is often over 350 mOsm.

In certain embodiments, the osmolarity is over 400 mOsm. In certain embodiments, the osmolarity is over 500 mOsm. In certain embodiments, the osmolarity is over 600 mOsm. In certain embodiments, the osmolarity is over 700 mOsm. In certain embodiments, the osmolarity is over 800 mOsm. In certain embodiments, the osmolarity is over 900 mOsm. In certain embodiments, the osmolarity is over 1000 mOsm.

In another embodiment, the composition or formulations described herein are formulated for delivery to various epithelial tissues. In some cases, the compositions and formulations are formulated as a topical that is applied to keratinized skin or mucous membranes of the eyes or genitourinary tract. Non-limiting examples, include, powders, drops, vapors, mists, sprays, foams, gels, emulsions, lotions, creams, ointments, pastes, liquid powders, semisolids, and solids.

In another embodiment, the above described compositions and formulations are used to treat acute pruritus, pain, or inflammation in a subject in need thereof by administering the compositions or formulations to the subject. In some cases, the acute pruritus, pain, or inflammation is due to or associated with allergies, insect bites, exposure to venom, poison ivy, atopic dermatitis, psoriasis, thermal burns, ionizing radiation, exposure to chemicals, trauma, surgery, nerve compression, oral or throat ulcers, bacterial infections, or viral infections.

In another embodiment, the above described compositions and formulations are used to treat chronic pruritus, pain, or inflammation in a subject in need thereof by administering the compositions or formulations to the subject. In some cases, the chronic pruritus, pain, or inflammation is due to or associated with atopic dermatitis, psoriasis, viral infections, nerve compression, back pain, amputation, or trauma.

In another embodiment, the above described compositions and formulations are used to treat neuropathic pruritus, pain, or inflammation in a subject in need thereof by administering the compositions or formulations to the subject. In some cases, the neuropathic pruritus, pain, or inflammation is due to or associated with post herpetic neuralgia, back pain, nerve compression, viral infections, multiple sclerosis, Parkinson's disease, diabetes, trauma, amputation, or drug use.

In another embodiment, the above described compositions and formulations are used to treat prevent or reverse a neuropathic condition in a subject in need thereof by administering the compositions or formulations to the subject. In some cases, the neuropathic condition is due to nerve compression, nerve over sensitization, stump pain, post herpetic neuralgia, shingles, diabetic neuropathy, arthritis, bacterial infections, viral infections, or drug use.

In another embodiment, the above described compositions and formulations are used to treat an epithelial wound in a subject in need thereof by administering the compositions or formulations to the subject. In some cases, the epithelial wound are skin plaques, dermatoses, scales, ulcers, rashes, burns, acne, cold sores, hives, canker sores, blisters, shingles, warts, or boils. In some cases, the wound are due to psoriasis, atopic dermatitis, eczema, bacteria, viruses, delayed type hypersensitivity, or allergies.

In another embodiment, the above described compositions and formulations are used to treat prevent or reduce damage in epithelial tissue in a subject in need thereof by administering the compositions or formulations to the subject. In some cases, the damage presents as a blister, a wart, a rash, or a hive. In some cases, the damage is due to a virus, a burn, an allergen, an insect bite, or a stinging critter.

In another embodiment, a topical formulation including, at a minimum, strontium and a carrier is used to treat post herpetic neuralgia in a subject in need thereof. In another embodiment, a topical formulation including, at a minimum, strontium and a carrier is used to treat, reduce, or prevent pain, itch, or inflammation associated with post herpetic neuralgia in a subject in need thereof. In another embodiment, the above described compositions and formulations are used to treat post herpetic neuralgia in a subject in need thereof. In another embodiment, the above described compositions and formulations are used to treat, reduce, or prevent pain, itch, or inflammation associated with post herpetic neuralgia in a subject in need thereof.

In another embodiment, a topical formulation including, at a minimum, strontium and a carrier is used to treat psoriasis in a subject in need thereof. In another embodiment, a topical formulation including, at a minimum, strontium and a carrier is used to treat, reduce, or prevent pain, itch, or inflammation associated with psoriasis in a subject in need thereof. In another embodiment, the above described compositions and formulations are used to treat psoriasis in a subject in need thereof. In another embodiment, the above described compositions and formulations are used to treat, reduce, or prevent pain, itch, or inflammation associated with psoriasis in a subject in need thereof.

In another embodiment, a topical formulation including, at a minimum, strontium and a carrier is used to treat diabetic neuropathy in a subject in need thereof. In another embodiment, a topical formulation including, at a minimum, strontium and a carrier is used to treat, reduce, or prevent pain, itch, or inflammation associated with diabetic neuropathy in a subject in need thereof. In another embodiment, the above described compositions and formulations are used to treat diabetic neuropathy in a subject in need thereof. In another embodiment, the above described compositions and formulations are used to treat, reduce, or prevent pain, itch, or inflammation associated with diabetic neuropathy in a subject in need thereof.

In another embodiment, a topical formulation including, at a minimum, strontium and a carrier is used to treat radiation dermatitis in a subject in need thereof. In another embodiment, a topical formulation including, at a minimum, strontium and a carrier is used to treat, reduce, or prevent pain, itch, or inflammation associated with radiation dermatitis in a subject in need thereof. In another embodiment, the above described compositions and formulations are used to treat radiation dermatitis in a subject in need thereof. In another embodiment, the above described compositions and formulations are used to treat, reduce, or prevent pain, itch, or inflammation associated with radiation dermatitis in a subject in need thereof.

In another embodiment, a topical formulation including, at a minimum, strontium and a carrier is used to treat atopic dermatitis in a subject in need thereof. In another embodiment, a topical formulation including, at a minimum, strontium and a carrier is used to treat, reduce, or prevent pain, itch, or inflammation associated atopic dermatitis in a subject in need thereof. In another embodiment, the above described compositions and formulations are used to treat atopic dermatitis in a subject in need thereof. In another embodiment, the above described compositions and formulations are used to treat, reduce, or prevent pain, itch, or inflammation associated with atopic dermatitis in a subject in need thereof.

In another embodiment, a topical formulation including, at a minimum, strontium and a carrier is used to treat restless leg syndrome in a subject in need thereof. In another embodiment, a topical formulation including, at a minimum, strontium and a carrier is used to treat, reduce, or prevent pain, itch, or irritation associated restless leg syndrome in a subject in need thereof. In another embodiment, the above described compositions and formulations are used to treat restless leg syndrome in a subject in need thereof. In another embodiment, the above described compositions and formulations are used to treat, reduce, or prevent pain, itch, or irritation associated with restless leg syndrome in a subject in need thereof.

In another embodiment, a topical formulation including, at a minimum, strontium and a carrier is used to treat joint pain in a subject in need thereof. In another embodiment, a topical formulation including, at a minimum, strontium and a carrier is used to treat, reduce, or prevent pain, itch, or inflammation associated joint pain in a subject in need thereof. In another embodiment, the above described compositions and formulations are used to treat joint pain in a subject in need thereof. In another embodiment, the above described compositions and formulations are used to treat, reduce, or prevent pain, itch, or inflammation associated with joint pain in a subject in need thereof. In one embodiment, the joint pain is in the fingers, wrists, elbows, shoulder, neck, knee, ankle, or toes.

In another embodiment, the above described compositions and formulations are used to treat a thermal, radiation, or chemical burn in a subject in need thereof. In another embodiment, the above described compositions and formulations are used to treat, reduce, or prevent pain, itch, or inflammation associated with a thermal, radiation, or chemical burn in a subject in need thereof. In another embodiment, the burn is a minor burn. In another embodiment, the burn is a major burn. In another embodiment, the above described compositions and formulations are part of a dressing used to cover the thermal, radiation, or chemical burn in a subject in need thereof.

In another embodiment, the above described compositions and formulations are used to treat a surgically closed wound or an amputation stump in a subject in need thereof. In another embodiment, the above described compositions and formulations are used to treat, reduce, or prevent pain, itch, or inflammation associated with a surgically closed wound or an amputation stump in a subject in need thereof. In another embodiment, the above described compositions and formulations are part of a dressing used to cover the surgically closed wound or amputation stump in a subject in need thereof.

In accordance with the teachings herein, the present disclosure relates generally to compositions of strontium-containing complexes in a suitable carrier vehicle. The complexes are bipartite or tripartite in nature, in that they include at least one or two different components: divalent cationic strontium, and at least one counterion, such as a beta hydroxybutyrate. In the form of a tripartite composition, the complexes include divalent cationic strontium, beta hydroxybutyrate, and at least one cysteine-based antioxidant.

The cysteine-based anti-oxidant may be selected from the group consisting of: cysteine, cystine, N-acetyl cysteine (NAC), N-acetyl cysteinate, N-acetyl cystine and N,S-diacetylcysteine, or mixtures thereof.

Either the bipartite or tripartite complexes may also be complexed with a polymer, such as a polyanionic polymer. This polymer may be s selected from the group consisting of: polyvinylpyrrolidone (PVP), cyclodextrins, carragenans, alginic acid, xanthan gum, sulfated polysaccharides, pentosan polysulfate, chondroitin sulfate, dextran sulfate and heparin sulfate.

The osmolarity of the compositions may beneficially have high osmotic activity, such as having an osmolarity equal to or greater than 400 mOsm, or between 400 and 2000 mOsm.

In an alternate embodiment of a tripartite composition, the at least one cysteine-based anti-oxidant and an aliphatic hydroxyacid (e.g., 2-hydroxybutanoic acid, which yields a beta hydroxybutyrate moiety) are conjugated together by a cleavable bond, such as a peptide bond, an ester bond, a thioester bond, an enzymatically cleavable bond, a disulfide bond, or a pH dependent bond.

In an alternate embodiment of a bipartite composition, the divalent cationic strontium is complexed with an aliphatic hydroxyacid (e.g., 2-hydroxybutanoic acid, which yields a beta hydroxybutyrate moiety) and the complex is placed in a suitable carrier vehicle prior to administration.

The compositions containing bipartite complexes can also include other constituents, such as any of the aforementioned strontium counter ions.

In another embodiment, a composition is provided comprising a complex of: a divalent cationic strontium moiety; a cysteine-based moiety selected from the group consisting of cystine, N-acetyl cysteine, N-acetyl cysteinate, N-acetyl cystine, N,S-diacetylcysteine, and esters thereof; and a beta hydroxybutyrate moiety; wherein the cysteine-based anti-oxidant and an aliphatic hydroxyacid moiety (e.g., beta hydroxybutyrate) are conjugated together by a cleavable bond. The cysteine-based anti-oxidant moiety can be N-acetyl cysteine or an ester thereof. The strontium moiety can be a strontium salt selected from the group consisting of strontium chloride, strontium chloride hexahydrate, strontium sulfate, strontium carbonate, strontium nitrate, strontium hydroxide, strontium hydrosulfide, strontium oxide, strontium acetate, strontium glutamate, strontium aspartate, strontium malonate, strontium maleate, strontium citrate, strontium threonate, strontium lactate, strontium pyruvate, strontium ascorbate, strontium alpha-ketoglutarate, and strontium succinate. The cleavable bond can be selected from the group consisting of a peptide bond, an ester bond, a thioester bond, an enzymatically cleavable bond, a disulfide bond, and a pH dependent bond. The cleavable bond can be a thioester bond. The composition can further comprise a polymer. The polymer can be selected from the group consisting of polyvinylpyrrolidone, cyclodextrins, carrageenan, alginic acid, xanthan gum, sulfated polysaccharides, pentosan polysulfate, chondroitin sulfate, dextran sulfate and heparin sulfate. The composition can be a complex of divalent cationic strontium, N-acetylcysteine or an ester thereof and beta hydroxybutyrate, wherein the N-acetylcysteine or an ester thereof and the beta hydroxybutyrate are conjugated together by a thioester bond formed by a sulfhydryl group of the N-acetylcysteine or an ester thereof and a carboxyl group of the beta hydroxybutyrate moiety.

In another embodiment, a formulation is provided comprising a complex and at least one pharmaceutically acceptable excipient, wherein the complex is of a divalent cationic strontium moiety; a cysteine-based moiety selected from the group consisting of cystine, N-acetyl cysteine, N-acetyl cysteinate, N-acetyl cystine, N,S-diacetylcysteine, and esters thereof; and a beta hydroxybutyrate moiety; wherein the cysteine-based anti-oxidant and the beta hydroxybutyrate moiety are conjugated together by a cleavable bond. The formulation can be configured for topical administration. The formulation can be configured for oral or systemic administration. The formulation can be configured for oral ingestion. The formulation can further comprise a polymer. The polymer can be a neutral or anionic polymer. The neutral polymer can be polyvinylpyrrolidone. The polyvinylpyrrolidone can be chemically modified by derivatization and/or crosslinking. The polymer can be configured for ionic association with the complex and facilitates controlled release of the divalent cationic strontium. The polymer can be configured for minimizing osmolarity. The formulation can further comprise at least one aromatic amino acid selected from the group consisting of histidine, tyrosine, phenylalanine and tryptophan. The at least one aromatic amino acid can be an L-isomer.

In another embodiment, a method is provided of treating pain in a patient in need thereof, comprising topically administering to the patient a composition comprising a complex of: a divalent cationic strontium moiety; a cysteine-based moiety selected from the group consisting of cystine, N-acetyl cysteine, N-acetyl cysteinate, N-acetyl cystine, N,S-diacetylcysteine, and esters thereof; and a aliphatic hydroxyacid moiety such as beta hydroxybutyrate or a similar moiety; wherein the cysteine-based anti-oxidant and the beta hydroxybutyrate moiety are conjugated together by a cleavable bond.

In another embodiment, a method is provided of treating pruritus in a patient in need thereof, comprising topically administering to the patient a composition comprising a complex of: a divalent cationic strontium moiety; a cysteine-based moiety selected from the group consisting of cystine, N-acetyl cysteine, N-acetyl cysteinate, N-acetyl cystine, N,S-diacetylcysteine, and esters thereof; and a beta hydroxybutyrate moiety; wherein the cysteine-based anti-oxidant and an aliphatic hydroxyacid moiety (e.g., beta hydroxybutyrate) are conjugated together by a cleavable bond.

In another embodiment, the above described compositions and formulations are applied post incident or after the development of the condition. In another embodiment, the above described compositions and formulations are used in a preventative manner. In another embodiment, the above described compositions and formulations are applied continuously.

For each of the above described treatments, the compositions or formulations are topically administered to epithelial tissue. The epithelial tissue is keratinized skin or mucous membranes in the eye, mouth, throat, esophagus, gastrointestinal tract, respiratory tract or genitourinary tract. In some embodiments, the compositions or formulations are administered using an applicator device. Often, the device is a patch, roller, syringe, dropper, sprayer, mister, or dressing.

DETAILED DESCRIPTION

The present disclosure relates to therapeutically-active compositions that combine strontium with a second compound that synergistically increases the overall therapeutic potency of the combination beyond the potency of any of the separate constituents. Specifically, the combinations described herein increase the ability of strontium to (1) inhibit acute sensory pruritus, pain, redness, swelling, and inflammation (collectively defined for purposes of this description, "irritation"), (2) inhibit chronic irritation that may contribute to the development and maintenance of painful or pruritic neuropathic conditions, (3) inhibit neuropathic irritation that may contribute to increased nerve sensitivity or reactivity, (4) break the neuropathic positive feedback cycle that contributes to neuropathic pain or itch, (5) promote healing in damaged epithelial tissue, and/or (6) minimize infection in a wound.

Definitions

In the description that follows, a number of terms are extensively utilized. The following non-limiting definitions provide a clear and consistent understanding of the specification and claims, including the exemplary scope to be given such terms. Unless defined otherwise, all technical and scientific terms used herein have the same meaning as is commonly understood by one of ordinary skill in the art to which this invention belongs.

The terms "invention" or "present invention" as used herein are intended to be non-limiting and are not intended to refer to any single embodiment of the particular invention but encompasses all possible embodiments as described in the specification and the claims.

As used herein, the term "and/or" may mean "and," it may mean "or," it may mean "exclusive-or," it may mean "one," it may mean "some, but not all," it may mean "neither," and/or it may mean "both."

The term "epithelial" or "epithelium" as used herein refers to outer surfaces of the body in the broadest sense of the word and therefore implicitly includes all keratinized tissue as well as mucous membranes, for example, the mouth, throat, surfaces of the eye, the respiratory tract, the gastrointestinal tract, and the genitourinary tract, including the cervix and the vagina.

The term "beneficial agent" as used herein refers to a chemical, compound, or ingredient that helps reduce pain, pruritus, or inflammation and/or promotes healing in epithelial tissue and/or improves fibrotic conditions. Beneficial agents may be chemicals or compounds that are either generally recognized as safe, approved by the U.S. Food and Drug Administration (or equivalent agency in other countries), or recognized by those skilled in the arts as being beneficial. Non-limiting examples of beneficial agents are described and listed herein, including analgesics, antihistamines, antibacterials, corticosteroids, moisturizers, vitamins, biologics, plant extracts, and polymers.

As used herein, "treatment" means any manner in which the symptoms of a condition, disorder or disease are ameliorated or otherwise beneficially altered. Treatment also encompasses any pharmaceutical use of the compositions herein.

As used herein, "subject" refers to an animal, including, but not limited to, a primate (e.g., human). The terms "subject" and "patient" are used interchangeably herein.

As used herein, the term "strontium-containing component" refers to either elemental strontium or a strontium salt. The terms "elemental strontium" and "strontium cation" are used interchangeably herein.

As used herein, the terms "moisturizer" and "skin protectant" are used interchangeably unless otherwise indicated.

The term "complex" as used herein refers to a combination of the strontium cation and two other negatively charged or polar molecules (strontium counterions) via either electrostatic forces (for example, due to the pi-electrons in the phenolic ring structures), or association with a partial negative charge or other inter-molecular charges. In addition to strontium and the two strontium counterions, the complex may also contain polymeric substances like polyvinylpyrrolidones, polyacrylamides, polyanionic polymers like alginic acid, carrageenans or carbohydrate polymers that have an inherent ability to reversibly bind to and complex with thiol-containing molecules like N-Acetyl-L-Cysteine (NAC), or aliphatic hydroxyacids such as a beta hydroxy-acid (e.g., beta-hydroxybutanoic acid or 3-hydroxybutanoic acid), polyhydroxyphenolic compounds like gallic acid, quercetin, luteolin, myricetin and other similar molecules.

The term "cysteine-based" anti-oxidant as used herein refers to cysteine, cysteine derivatives, cysteine-containing small (less than four amino acids) peptides and cysteine precursors.

The term "cleavable" means a covalent chemical bond that is capable of being broken. "Cleavable" only requires that a fraction of the chemical bonds are cleaved, that is, the chemical bonds are cleavable if a portion of the bonds are cleaved. In one instance, the bond is cleavable within the skin after administration.

The term "conjugated" means a compound where at least two of the components are joined together with a cleavable bond.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. 11:942-944 (1972)).

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of phosphate groups are intended to be included. Furthermore, all tautomers of heterocyclic bases known in the art are intended to be included, including tautomers of natural and non-natural purine-bases and pyrimidine-bases.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless the context indicates otherwise. Similarly, a group of items linked with the conjunction 'or' should not be read as requiring mutual exclusivity among that group, but rather should be read as 'and/or' unless the context indicates otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

Where a range of values is provided, it is understood that the upper and lower limit, and each intervening value between the upper and lower limit of the range is encompassed within the embodiments.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained.

At the very least, and not as an attempt to limit the application of the doctrine of equivalents to the scope of any claims in any application claiming priority to the present application, each numerical parameter should be construed in light of the number of significant digits and ordinary rounding approaches.

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element in a compound may be any isotope of said element. Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like.

Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

The term "salt" as used herein is a broad term and includes without limitation pharmaceutically acceptable salts such as a salt of a compound that does not cause significant harm to an organism to which it is administered and does not abrogate the biological activity and properties of the compound. In some embodiments, the salt is an acid addition salt of the compound. Pharmaceutical salts can be obtained by reacting a compound with an inorganic acid, an organic acid, or a base. Suitable pharmaceutically acceptable salts include metallic salts, organic salts, salts of free acids and bases, inorganic salts, and other salts which are currently in widespread pharmaceutical use and are listed in sources well known to those of skill in the art, such as, for example, The Merck Index.

Nociception and Inflammation Pathways

Nociception involves the neural processes of encoding and processing stimuli that have the potential to damage tissue. Nociceptors are specialized nerves located throughout the body that detect mechanical, thermal or chemical changes. There are two classes of nociceptors, the first class is "A-delta" nerves, which respond to physical trauma by transmitting a pain sensation with a sharp, pricking quality. The second class is "Type C" nerves (TCN), which are chemical sensors that respond to irritants from our environment, such as microbes, temperature extremes, and ionizing radiation and transmit diffuse sensations of burning pain, stinging pain or itching ("irritation"). When excessively stimulated, TCN can also release neuropeptides (e.g., Substance P) that directly activate histamine-containing mast cells and attract and activate other immune system cells such as neutrophils that cause redness, swelling and even local tissue damage. After activation by a stimulus, nociceptors synapse near the spinal cord in the dorsal root ganglia (DRG) and release neurotransmitters that activate nerve pathways that relay signals to the brain. The brain interprets the signals as various types of pain or itch.

A. Acute, Chronic, and Neuropathic Pain and Pruritus Occur Upon Nociceptor Activation Exposure to stimuli activates nociceptors. Depending on the stimuli, both types of nociceptors may be activated or in many instances either the A-delta or TCN are preferentially activated. Since only the TCNs extend to the outermost portions of the body, such as the skin, mouth, nose, throat, eyes, etc. (herein referred to as "epithelium" or "epidermis") and may be activated by virtually any process that changes the local biochemistry of the epidermis, TCNs are preferentially activated in response to most irritating stimuli. Upon activation of TCNs in the skin, the TCNs transmit a signal to the spinal cord and trigger neurotransmitter release in the DRG that activate nerves in the spinal cord that relay the pain and itch signals to the brain.

Acute activation of TCNs that is caused by exposure to a chemical irritant, trauma or a sunburn typically causes painful or pruritic sensations that last only several days and is termed "nociceptive pain". When the stimulus is prolonged or excessively severe as can occur after a viral disease like shingles or HIV, or the nerves are damaged by trauma to nerves from physical pressure, thermal burns, diabetes or extensive physical trauma to a limb, painful sensations or pruritus can continue for many years. Such chronic pain or pruritus caused by excessive nociceptor activation or damage is termed "neuropathic" and is among one of the most difficult conditions to treat. Even the best oral or topical drugs have only a very limited therapeutic benefit and many have substantial side effects that limit their use.

B. Nociceptive Signals are Typically Encoded as Precisely-Timed Changes of Intracellular Calcium Concentration that Travel as "Calcium Waves" within Nociceptors No matter what causes nociceptor activation, the event is encoded into a universal code; a complex change in the intracellular calcium concentration that, in turn, is transmitted throughout the nociceptor. Calcium thus acts as a universal "second messenger" and information transmitted by a nociceptor, including the intensity and quality of pain or pruritus is converted into a language made up of rapidly changing calcium concentrations. Since nerves in general and nociceptors in particular transmit their calcium code typically within about $1/1000$th of a second, the timing and spatial distribution of calcium must be exquisitely regulated to accurately transmit the encoded information. In virtually all nerves, including nociceptors, the intensity of the signal (e.g., the severity of pain or pruritus) is encoded as a change in frequency of calcium waves that trigger neurotransmitters that are released into the synapse and activate post-synaptic nerves that relay the information ultimately to the brain. The higher the frequency, the more intense the perceived sensation. When a nociceptor is activated, the calcium signal is transmitted through multiple biochemical pathways, many of which operate in sequence such that the output of one pathway becomes the input of the next.

Activation of the nociceptor triggers the release of neurotransmitters, namely glutamic acid, substance P, and adenosine triphosphate (ATP). The frequency of nociceptor activation determines which neurotransmitter is released by the TCN. Under low frequency, only glutamic acid is released. Under high frequency, both glutamic acid and substance P are released Glutamic acid and substance P have a synergistic effect to increase pain, itch, and inflammation.

Glutamic acid is the most widely used excitatory neurotransmitter in the central and periphery nervous system and is a pain and itch activator. Glutamic acid functions as a neurotransmitter in two distinct manners. The first is as a point-to-point transmitter and the second is through spillover synaptic crosstalk between synapses. When synaptic crosstalk occurs, the combined amount of glutamic acid released from the neighboring synapse creates extrasynaptic signaling/volume transmission. Glutamic acid is stored in vesicles near the synaptic junction. As mentioned above activation of the nociceptor triggers the release of glutamic acid where it acts on ionotropic and metabotropic (G-protein coupled) receptors. After glutamic acid is released, several different glutamic acid transporters rapidly clear the glutamic acid from the extracellular space thereby ending the synaptic transmission. The main glutamic acid transporters are excitatory amino acid transporters (EAAT 1-5), vesicular glutamate transporters (VGLUT 1-3), and cystine-glutamate antiporter (xCT). EAATs are dependent on the electrochemical gradients of ions such as sodium, potassium, or hydrogen whereas VGLUT and xCT are not. xCT is localized to the plasma membrane of cells while VGLUT is found in the membrane of glutamate-containing synaptic vesicles. VGLUTs repackage glutamic acid into vesicles using an acid (hydrogen ion) gradient. Vesicular ATPase use ATP to acidify the vesicle. The resulting pH gradient is then used to drive a calcium hydrogen (Ca/H) antiporter, which transports glutamic acid into the vesicle.

Substance P is part of a family of neuropeptides commonly referred to as tachykinins or neurokinins. The release of substance P is a complex process involving several intracellular effectors such as extracellular calcium influx, 1,4,5-inositol triphosphate-induced calcium release, activation of extracellular signal-regulated kinase (ERK), cyclooxygenases (COX), prostaglandins, and cyclic AMP-dependent protein kinas A (PKA). Substance P binds to G-protein coupled receptors, neurokinin 1, 2, and 3 (NK). Activation of the NK receptors activated several messenger system including phospholipase C (PLC), adenylate cyclate, ERK1/2, p38, mitogen-activated protein (MAP) kinases, nuclear factor-kappa B (NFKB) and protein kinase C (PKC). Activation of the secondary messenger systems results in an increase 1,4,5-inositol trisphosphate, cyclic AMP, prostaglandin E2 and COX-2. Substance P also activated several immune cells including keratinocytes, neutrophils, B-cells, T-cells, and others. Substance P also sensitized other cells to release and activate interleukin 8 (IL-8) and leukotriene B4, both of which activate neutrophils and begin the neutrophil feedback loop as neutrophils also release leukotriene B4.

As mentioned above, substance P is only released under high frequency nerve stimulation. The amount of substance P released is proportional to the intensity and frequency of the stimulation. When released in high amounts, Substance P has the capability of diffusing and binding to NK1 receptors on nearby neurons. Substance P is also secreted by inflammatory cells such as macrophages, eosinophils, lymphocytes, and dendritic cells.

Upon binding by substance P, the NK1 receptor undergoes clathrin mediated endocytosis in which the bound receptor and other signaling molecules are incased in a lipid endosome. The resulting signaling endosome further activates other pathways including mitogen activated protein kinases (MAPK). The mitogen activated protein kinases (MAPK) are involved in directing cellular responses to a diverse array of stimuli, such as mitogens, osmotic stress, heat shock and inflammation. The MAPK family consists of three major members: extracellular signal-regulated kinases 1 and 2 (ERK-1/2), p38, and c-Jun N-terminal kinase (JNK), each of which represents a separate signaling pathways. Accumulating evidence shows that all three MAPK pathways can contribute to pain sensitization after tissue and nerve injury via distinct molecular and cellular mechanisms. Activation of ERK-1/2, p38, and JNK leads to the synthesis of proinflammatory and/or pronociceptive mediators, which can result in enhanced and prolonged pain.

MAPKs can be activated at either the cell membrane or in the cytosol. Once activated, MAPKs can phosphorylate proteins in both the cytosol and nucleus. Thus, MAPKs can relay extracellular stimuli from the plasma membrane to cellular targets distant from the membrane, such as transcription factors, initiating diverse cellular responses. In some pathways, it is believed that activated MAPKs undergo endocytosis to allow rapid transport to remote locations (e.g. nuclease) to facilitate the propagation of signals to remote cellular locations.

ATP is a neurotransmitter in the periphery nervous system. Similar to glutamic acid and substance P, it is also stored in vesicles. Frequently, ATP is also found co-stored in a single vesicle with other neurotransmitters, possibly serving as a neurotransmitter and/or an energy source upon vesicle exocytosis. Similar to glutamic acid, ATP is loaded into the vesicles using a hydrogen ion gradient. Vesicular nucleotide transporter (VNUT) use the hydrogen ion gradient to move ATP into the vesicle. Also similar to glutamic acid, the hydrogen ion gradient is created using a calcium/hydrogen antiporter.

C. Nociceptive Signals and the Biochemical Pathways That Encode Signals Have an Output That is Logarithmically Related to the Input The many nociceptor pathways as well as the overall neurotransmitter release by a nociceptor are typically logarithmically related to the intensity of the stimulus. For example, if the irritant caused the nociceptor activation to increase its frequency of activation, also called depolarization, from 10 to 50 per second, the frequency of the resultant neurotransmitter release may only increase by a factor of 1.7 (Log 10=1.0; Log 50=1.7). This fact is particularly relevant since it indicates that a relatively small amount of inhibition of a nociceptor's activation can cause a large reduction in the perceived severity of the painful or pruritic stimulus. Since there are many separate pathways in nociceptors that act in sequence to encode and transmit an irritant stimulus, inhibiting each of the sequential pathways at one or more of a pathway's steps has the potential to produce a very large cumulative reduction of the painful or pruritic sensation.

D. The Development and Maintenance of Neuropathic Pain or Pruritus Requires Excessive and Continuous Nociceptor Activation In order for a neuropathic condition to develop, nociceptors must be continuously activated by a potent stimulus. The duration of the activation required may substantially vary depending on the specific nerve injury or stimulant. When such activation occurs, the peripheral nociceptors that innervate the skin and mucous membranes may become sensitized within hours and may continue to increase their sensitivity to irritants and may even be activated by stimuli that are normally not irritating. Infections such as HIV or Herpes viruses, or chronic colonization by bacteria such as *Staphylococcus aureus* that is present at excessive levels on the skin of atopic dermatitis patients, burn patients, and patients suffering from ionizing radiation or traumatic damage to a nerve are especially potent nociceptor sensitizers. Release of multiple inflammatory mediators that accompany any trauma or inflammation are also important contributors to sensitization.

In order to establish a neuropathic state, sensory nerves in the DRG that receive sensory input from the TCN must also become sensitized ("central sensitization"). As for the peripheral TCN, the central neurons require sustained, high intensity activation for an extended period of time that may be as short as several days or much longer. The presence of inflammation, infectious agents, or trauma can accelerate the sensitized, neuropathic state. Due to neuronal "cross-talk," it is common for an initially small painful portion of sensitized tissue, for example, as occurs in post-herpetic neuralgia, to expand to the adjacent tissue via nociceptors that were uninjured, including A-delta nociceptors. Sensitized neuropathic tissue may also generate painful stimuli in response to mechanical pressure, e.g. coughing or swallowing, or temperature changes, a condition known as allodynia.

The sensitized state in both the peripheral nociceptors and their central counterparts is a form of activity-dependent plasticity that is very similar to the neurons in the CNS that form memories. In the case of neuropathic pain or pruritus, the nociceptive response produces a "memory of pain or itching." The molecules and pathways that produce the long-lasting neuronal sensitization are reasonably well defined. In particular, the activation of intracellular kinases. Of particular importance are protein kinase A and C (PKA and PKC, respectively), each of which exist in several different forms and the mitogen activated protein kinases (MAPK) that include the p38 MAPK, ERK-1/2 MAPK and the JNK MAPK. These kinases are activated by a broad range of environmental "danger signals" and internal cytokines and growth factors exposures including ionizing radiation, reactive oxygen species (ROS) always accompany infection and trauma. When activated, these kinases are activated in multiple pathways and give rise to sequential cascades that result in regulation and activation of genes that regulate well over 100 different molecules that activate immune cells, produce inflammation and molecules that influence ion channels and molecular sensors that cause the peripheral and central nociceptor sensitization that causes neuropathic pain and pruritus. Among these inflammation and immune-system activating genes, the most important is called Nuclear Factor, Immunoglobulin Light Chain Kappa, Enhancer of B Cells, abbreviated NF-Kappa B, called the "Master Gene Regulator of Inflammation." Additionally, some of these kinases like PKC can directly sensitize and activate nociceptors that cause calcium influx and interfere with strontium's ability to alter the calcium dynamics that occur in neuropathic states.

There are many causes of neuropathies, some of which are very common. For example, common neuropathies include viral infection (e.g., HIV, the Herpes varicella zoster virus (VZV) that causes chicken pox and in later years, or secondary to immunosuppression, shingles and for many, post-herpetic neuralgia, an intensely painful condition that typically occurs in advanced age). Diabetes is the most common cause of the typical burning pain due to glucose-induced nerve damage, serious burns, severe trauma or amputation and a number of drugs, especially some that are used to treat HIV. While there are oral drugs available like gabapentin (e.g. NEURONTIN®) and pregabalin (e.g. LYRICA®) that can provide significant relief from neuropathic symptoms, they all have potentially significant side effects such as somnolence, dizziness and changes in mentation in more than 25% of patients. Since many neuropathic patients are in their 70s or 80s and already have health limitations, these side effects can be particularly problematic and potentially dangerous. This frequently leads to reduced compliance with the required dosing schedule and thus reduced patient benefit.

E. Stimuli That Oxidize Intracellular Glutathione Trigger Multiple Nociceptor-Activating Pathways Of the many conditions that may cause nociceptor activation during the development of neuropathic conditions, the redox state of a nociceptor can produce some of the most potent acute and chronic nociceptor activating stimuli that exist. One of the most important regulatory signals that cause a cell to convert to a defensive state in which multiple inflammatory and cell protective immune activators are activated is the intracellular ratio of reduced glutathione (GSH) to oxidized glutathione (GSSG). Glutathione is the most plentiful intracellular thiol antioxidant, and is among the most important signal generators that trigger a cell to synthesize powerful inflammatory mediators and activate genes that, in turn, activate virtually every immune system inflammatory cell. The ratio of reduced glutathione, GSH, to the oxidized form, GSSG, is normally 9 to 1 or more. When cells are exposed to trauma, infection, inflammation or inflammatory mediators, ionizing radiation or general "cellular stress," the amount of reduced glutathione plummets and directly trigger multiple cascades of gene activation that ultimately lead to the synthesis of well over 100 inflammatory mediators, pro-inflammatory cytokines (e.g., TNF-alpha, IL-1, IL-6 and many others), and cytokines that attract and activate inflammatory immune cells, all of which sensitize and activate nociceptors that transmit pain and pruritic signals, and in turn amplify these inflammatory cascades by neurogenic inflammatory pathways. Many of the most important cellular regulators of inflammation and immune defense are highly sensitive to a reduction in a cell's GSH concentration, and are directly activated by a low GSH/GSSG ratio indicating that a cell is in an oxidative redox state.

Perhaps the most important of these redox-sensitive regulatory pathways is NF-Kappa B. This molecule is responsible for directly or indirectly inducing the synthesis of the most important and powerful inflammation activators, including TNF-alpha and many of the inflammatory interleukins and chemokines that attract inflammatory cells that secrete mediators that directly activate nociceptors and thus increase their long-term sensitization and conversion to a neuropathic state.

Since NF-Kappa B acts as a "final common pathway" for activation of multiple inflammatory pathways, substances that reduce or block NF-Kappa B activation will have substantial and broad anti-inflammatory activity and will block many forms of immune system-mediated activation of inflammatory pathways. NF-Kappa B is also one of the many regulatory molecules that is directly activated by an oxidative intracellular environment—one in which the ratio of reduced glutathione (GSH) to oxidized glutathione (GSSG) is minimized. This oxidative environment directly activates NF-Kappa B that greatly increases the synthesis of nociceptor-activating mediators and cytokines.

Since both peripheral nociceptors with endings in the epithelium and central nociceptors in the DRG and spinal cord become sensitized upon continuous activation, activation of NF-Kappa B is an important and critical stimulator of neuropathic sensitization.

F. Activation of Toll-Like Receptors by Microbes Activate Gene Transcription by NF-Kappa B That Sensitizes Activate Nociceptors Epidermal cells (e.g. keratinocytes), mucosal cells, and virtually all inflammatory immune cells have many receptors that can cause nociceptor activation. Among the most important are Toll-Like Receptors (TLRs), molecules that recognize conserved molecular structures of bacteria, fungi and viruses. TLRs bind to molecular structures called pathogen-associated molecular patterns (PAMPs) that are present in bacteria, protozoa, fungi, and viruses. Upon activation, TLRs trigger multiple inflammatory and nociceptor activating pathways, all of which lead to NF-Kappa B activation.

The present disclosure is based on the belief that certain conditions exhibit increased levels of bacteria on the skin. For example, patients with atopic dermatitis or eczema have 100 times higher level of *Staphylococcus aureus* on their skin when compared to patients without atopic dermatitis. Similarly, diabetic patients also tend to experience overgrowth of skin bacteria. The high levels of skin bacteria activate TLRs, which in turn activate multiple inflammatory and nociceptor pathways and result in the patient experiencing pain, itch, and irritation.

G. Activation of Inflammation Pathways by Viruses

The present disclosure is also based on the belief that many viruses, including herpes simplex virus (HSV), HIV, hepatitis, Epstein bar, influenza, adenovirus, and cytomegalovirus require the activation of NF-Kappa B to infect host cells. Post infection, some viruses also use the NF-Kappa B pathway either for its antiapoptotic properties to evade the host defense mechanisms or to trigger apoptosis as a mechanism of virus spread. For example, HSV activates NF-Kappa B in two distinct phases; the initial phase is during viral absorption and the second phase is during the de novo synthesis of viral proteins.

H. Activation of NF-Kappa B Produces Chemokines That Attract Inflammatory Cells

One of the most important consequences of NF-Kappa B is to stimulate the production of chemokines, including IL-8, that attract and activate neutrophils, a blood-borne white blood cell (WBC) that typically constitutes over 50% of all WBCs in the blood.

Neutrophils are the first responders to any type of trauma, infection or inflammatory process and accumulate at the triggering site in massive quantities. Upon activation by IL-8 and other inflammatory mediators, neutrophils produce massive levels of powerful oxidants, reactive oxygen species (ROS; e.g., superoxide, hydrogen peroxide, nitric oxide and hypochlorous acid) that rapidly deplete GSH from cells, including nociceptors, thus promoting oxidative activation of NF-Kappa B and activation of many kinases, including protein kinase A, protein kinase C and mitogen-activated protein kinases that act to amplify virtually all inflammatory pathways that directly activate nociceptors.

Activation of these multiple independent inflammatory pathways and inflammatory cells result in intense activation of nociceptors that contribute to the development of neuropathic sensitization and neuropathic pain and pruritus.

Such activation of nociceptors also causes them to release Substance P that directly triggers mast cell activation and release of histamine, TNF-alpha, IL-1, IL-6, IL-8 and many more inflammatory substances that further activate nociceptors. Due to the simultaneous activation of multiple inflammatory and nociceptor-activating pathways, there is a net amplification of nociceptor activation that is known to directly lead no neuropathic pain and pruritus.

Strontium Affects Nociception and Inflammation Pathways

Strontium's unique therapeutic properties are due to its chemical resemblance to calcium, the most important and universal "second messenger" in nerves and in all other cells that regulate virtually all cellular functions. The calcium ion always has two positive charges and its ionic radius is 0.99 angstroms, about the size of a hydrogen atom. Of all the elements, strontium most closely resembles calcium, since it also only exists as a divalent positively-charged ion and has an ionic radius of 1.13 angstroms. For this reason, strontium typically binds to calcium-binding sites and mimics calcium's activity. Most often a strontium-induced response is less potent and may be as low as about 1/1000th as active as calcium, but for certain calcium-dependent activities, strontium has activity that is nearly the same as calcium or in the range of 1/10th to 1/30th as active as calcium. In other calcium-dependent activities, strontium can be more active than calcium. It is strontium's calcium-mimetic activity that enables strontium to produce its many and varied activities. Since calcium is critical for so many cellular functions, if it were strongly inhibited the effects would be toxic to a cell. In contrast, since strontium can typically substitute for calcium, albeit with lower activity, the activity of the calcium-dependent pathway will not be shut down. Instead, the pathway activity will be reduced, similar to turning down the volume control of a radio. Since strontium, in a metaphoric sense, only turns down the volume control of calcium-dependent pathways rather than shutting down such pathways, the chances of significant adverse reactions or toxicity is much reduced compared to a drug that completely blocks a pathway.

A. Strontium Alters the Dynamics and Spatial Distribution of Calcium Waves

When irritants from chemicals, disease, trauma or other exposures activate receptors on the surface of TCNs that encode the intensity of their response as rapid changes in intracellular calcium concentrations, these changes can occur in less than 1/1000th of a second and produce highly complex "waves" of changing calcium concentration that propagate through the nerve and triggered most, if not all, of the pathways that cause acute, chronic and neuropathic irritation. In addition to the frequency of calcium waves, alterations in the dynamics of calcium concentration change the duration, magnitude and the precise shape of the calcium waveform that alters the coexisting electrostatic field that is a critical regulator of TCN activity. These changes independently activate the release of multiple inflammatory mediators, including prostaglandins (e.g., PGE2), leukotrienes (e.g., LTB4, C4, D4, and E4) and reactive oxygen species (ROS) including superoxide, hydrogen peroxide, hydroxyl radicals, hypochlorous acid and peroxynitrite.

Strontium thus significantly alters the pain and itch sensations encoded within calcium waves present in painful and pruritic neuropathic conditions, and has the effect of distorting the signal and reducing its perceived intensity by the brain. Due to strontium binding to multiple calcium-dependent signaling pathways, strontium significantly alters calcium-encoded signals by multiple independent mechanisms. Some of the calcium-dependent kinases are known to be essential for the development of neuropathic conditions, since their inhibition in animal models can prevent and or reverse established neuropathic conditions.

Strontium is not able to bind effectively to the calcium binding proteins within the cytoplasmic interior of nociceptors that normally remove calcium within less than a millisecond after calcium enters the nociceptor, thus producing a transient increase in calcium concentration that contributes to the precisely-timed calcium waves. Strontium is also much less effectively pumped into and released from a nociceptor's primary calcium storage site, the endoplasmic reticulum (ER). When a nociceptor-activating signal is received, strontium inhibits the calcium-induced calcium release (CICR) pathway that amplifies the calcium signal, and strontium does not have the ability to regulate inositol triphosphate (IP3)-induced calcium release by acting to inhibit additional calcium release if the concentration of calcium in the cytoplasm is too high.

Once calcium enters a nociceptor during its activation and depolarization, it activates the release of a massive amount of calcium that is stored in the ER by the CICR pathway. This mechanism has the effect of greatly amplifying the amount of calcium that is available to form a wave and to regulate calcium-dependent pathways. Strontium is over a hundred-fold less active than calcium in its ability to induce CICR and thus significantly alters the calcium concentration changes that normally occur in response to irritants. When in the ER, strontium also binds much less avidly to the ER calcium binding proteins that act as buffers and sequester the free calcium until it is released by CICR or other similar mechanisms. As a result, strontium reaches a concentration of more than 150% greater than calcium and displaces calcium from performing its amplifying function during CICR. Strontium is also much less active then calcium in regulating a second important calcium amplifying mechanism triggered by IP3, a ubiquitous substance that also activates calcium release from the ER by an IP3-specific receptor. At low concentrations of calcium, IP3 acts as a potent stimulator of calcium release that acts to amplify the much smaller calcium influx during depolarization. When the calcium concentration is sufficiently elevated, calcium acts to inhibit further calcium release thus maintaining the calcium concentration within a limited concentration range. When strontium is present, it can mimic calcium in its ability to activate IP3-induced calcium release, but strontium is not able to inhibit excessive calcium release causing both calcium and strontium to reach higher concentrations over an extended time. Strontium's ability to substantially inhibit calcium-induced release due to IP3 is particularly important, since IP3-induced calcium release is known to be responsible for generation of calcium waves. These types of strontium effects significantly change the calcium dynamics and calcium waveforms associated with neuropathic conditions, and thus contribute to strontium's suppressive effects on pain and pruritus.

B. Strontium Inhibits Calcium-Dependent Neurotransmitter Release

While strontium also affects additional pathways that control the dynamics of calcium within nociceptors, there is one strontium-induced interference with calcium-dependent transmission of pain and itch-encoded calcium waves that is critically important for suppression of acute, chronic, and neuropathic conditions. That is, the ability of strontium to bind and inactivate synaptotagmin-1, a molecule that is principally responsible for neurotransmitter release in the DRG. Other members of the synaptotagmin molecular superfamily and related calcium-regulated molecules regulate the release of inflammatory neuropeptides, including substance P from the peripheral portion of a TCN in the epithelium. Substance P is known to be the most important inflammatory neuropeptide released from TCNs that activates virtually every inflammatory immune "white blood cell" (WBC), including mast cells that contain histamine and over 50 different inflammatory chemicals, including tumor necrosis factor-alpha (TNF-alpha), interleukin 1 alpha and beta (IL-1 alpha and beta) and IL-6. These three pro-inflammatory cytokines are believed to be the "first responders" that directly activate TCNs to cause pain and/or itching and are thought to be significant contributors to the development and maintenance of neuropathic conditions, as well as most skin conditions that are associated with inflammation, pain or itching.

Synaptotagmin-1 is a protein present on the surface of vesicles that contain and ultimately release neurotransmitters that bind to the post-synaptic neurons in the DRG and the peripheral TCN endings in the epithelium that relay the pain and itch-encoded signals to the brain. Normally, the frequency of the presynaptic neurotransmitter release from nociceptors are precisely matched so that the intensity, timing and other properties of the original pain or itch signal encoded in the calcium wave is accurately transmitted to the brain. The delay between the arrival of the calcium wave, neurotransmitter release and post-synaptic activation is usually about 1/1000$^{th}$ of a second and the amount released is related to the intensity of the original TCN signal. This type of neurotransmission is termed "synchronous release," since the timing of the arrival of the calcium wave is tightly synchronized to the release of neurotransmitters that triggers post-synaptic activation of the DRG nerve. Without this precise coupling, the frequency encoded pain or itch signal becomes distorted.

When strontium substitutes for calcium, the amplitude of synchronous neurotransmitter release in response to TCN activation is typically reduced by more than 90%. Strontium has an additional signal distorting effect that significantly distorts the timing of neurotransmitter release called "asynchronous release." In contrast to synchronous release that is tightly coupled to the stimulating signal, asynchronous release may extend to several hundred milliseconds. With strontium, the total amount of neurotransmitter that is released may be the same as with calcium, however the strength of the synchronous release that contains the encoded pain or itch intensity information is strongly reduced, and the critical timing information is essentially destroyed. This strontium mechanism not only reduces the perceived severity of a pain or itch signal, but it also suppresses the release of substance P at the proximal end of the TCN in the epithelium at the original site of TCN activation. Strontium's ability to inhibit the release of TNF-alpha, IL-alpha and IL-6 is probably due to a similar interference of synaptotagmin or related calcium release mechanisms since it is the secretory mechanism used by virtually every cell. Suppression of synchronous neurotransmitter release also has an important therapeutic benefit for neuropathic pain or pruritus treatment.

Accordingly, in one embodiment, it is therefore desirable to further alter the calcium dynamics of nociceptors by further suppressing calcium release or by interfering with critical calcium-dependent pathways that are partially inhibited by strontium.

C. Strontium Binds to a Calcium-Sensing Receptor on Nociceptors That Suppresses Nociceptor Activation Most, if not all, cells have a recently-identified surface receptor (CaSR) that detects extracellular calcium concentration. Strontium also binds and activates the CaSR receptor as efficiently as calcium, but triggers additional activities. In view of this, a simple strontium salt was commercially developed, strontium ranelate, which is an orally administered prescription drug for osteoporosis treatment in over 100 countries. Due to strontium's unique ability to mimic calcium's ability to activate the CaSR and, additionally, to activate additional pathways linked to the CaSR, strontium ranelate is the only known osteoporosis drug that has two independent osteoporosis therapeutic mechanisms—strontium inhibits bone loss by inhibiting bone-resorbing osteoclasts, and simultaneously stimulates osteoblasts that produce new bone.

Nociceptors also have a CaSR that inhibits nociceptor activation when the extracellular concentration of calcium is raised above normal, or if a similar concentration of strontium is administered. Though not wishing to be bound by any particular theory of operation, this mechanism is believed to contribute to the ability of strontium to rapidly inhibit TCN activation by, for example, highly acidic chemical peels such as 70% glycolic acid, pH 0.6, that cause burning pain within seconds after application. When strontium is mixed with the acid, burning pain and stinging is suppressed by 80% or more so that any remaining sensory irritation is not bothersome.

Activation of the CaSR also causes activation of several pathways that are known to increase both acute, chronic and neuropathic pain and pruritus and inflammation. Since in real world use, strontium typically inhibits pain and pruritus, it is likely that the pain and itch enhancing effect caused by activation of the CaSR by strontium is, in effect, negated by other strontium anti-irritant mechanisms. None the less, even a low level, "subclinical" pain and itch-enhancing effect reduces the ability of strontium to effectively treat, prevent or reverse neuropathic conditions for which any excess TCN activation is known to promote the neuropathic condition.

Of particular concern is strontium's reported ability to bind to the CaSR and rapidly activate two of the MAPK molecules, p38 and ERK-1/2, that are known to be among the primary contributors to peripheral and central nociceptor sensitization. Strontium binding to the CaSR is also reported to activate an important enzyme, phospholipase C, that produces two important regulatory molecules, the aforementioned IP3, and diacylglycerol (DAG), both of which contribute to nociceptor activation and sensitization and inflammation. IP3 is one of the most important and potent calcium releasing molecules that directly trigger calcium release from ER stores. Many of the pain and itch producing chemicals that are produced during inflammation, infection or trauma use the IP3 pathway to activate nociceptors and produce the calcium waves that transmit pain and itch sensations. DAG is the principle activator of Protein Kinase C (PKC), a family of molecules that directly activates nociceptors and many of the pathways that produce pain and itch and inflammatory mediators. PKC is also known to be an important nociceptor sensitizer, since PKC inhibition can prevent or reverse neuropathic pain in animal models. PKC also activates NF-Kappa B, one of the most important stimulators of molecules that triggers pain, pruritus and inflammation and are thought to be able to directly cause neuropathic sensitization. It should be emphasized that the recognition that strontium produces its osteoporosis therapeutic benefits by binding to the CaSR is very recent and additional strontium-sensitive pathways will likely be identified. The fact that human nociceptors have the CaSR that regulate nociceptor activation suggests that the CaSR activation by topically-applied strontium may be working at a reduced level due to strontium's ability to inhibit important pain and itch pathways while simultaneously activating pathways via the CaSR that are known to trigger pain and itch pathways. Most importantly, since activation of these CaSR pathways is known to contribute to the development of neuropathic conditions, strontium's therapeutic potential may be substantially compromised.

Accordingly, in one embodiment, it is therefore desirable to create strontium-based formulations, e.g., salts or complexes, that have molecular components that specifically inhibit the CaSR pathways known to enhance neuropathic pain, pruritus and inflammation.

It is one object of the present disclosure to inhibit multiple nociceptor pathways by combining strontium with other molecules that specifically target pathways that are regulated by strontium and produce an overall reduction in pain or pruritus or other benefits to a patient, such as preventing or reversing a neuropathic pain or pruritic condition. It is another object of the present disclosure to combine strontium with other molecules that also cause inhibition or stimulation of strontium regulated pathways, but a different steps than those regulated by strontium. It is important to note that some nociceptor pathways are inherently inhibitory and if inhibited, the overall result may be stimulation of the nociceptor. For this reason, the term "strontium-regulated pathway" will be used to denote the fact that the overall effect of strontium or the molecules that are to be combined with strontium may either stimulate or inhibit a particular nociceptor pathway. It is another object of the present disclosure to combine strontium and additional molecules in a chemical manner that causes strontium and the molecules to chemically combine as a "salt" or "complex," for example a high molecular weight polymer such as polyanionic polymers such as alginic acid, carrageenan or other polymers that can form a matrix with strontium and the additional strontium-regulating molecules. By creating strontium salts or complexes, the osmolarity of a formulation will be reduced in comparison to having a strontium and two inactive counterions to balance strontium's two positive charges.

D. Strontium Inhibits NF-Kappa B

As mentioned above, bacteria and viruses on the skin activate various inflammatory pathways such as TLRs. TLR's ultimately activate NF-Kappa B. By shutting down NF-Kappa B, strontium can prevent the activation of the immune system E. Strontium Blocks Packaging and Endocytosis of Vesicles Without wishing to be bound by any one theory, it is believed that strontium affects the packaging and formation of endocytotic vesicles by blocking or reducing the activity at least two separate mechanisms. The first mechanism is VGLUT-2, which is used to package glutamic acid into vesicles and the second mechanism is dynamin, which is used to pinch off the endocytotic vesicle from the membrane. Each mechanism is discussed briefly below.

As mentioned above, glutamic acid and ATP are packaged and stored in vesicles.

VGLUT and VNUT pump glutamic acid and ATP, respectively, into the vesicle by using the hydrogen gradient created by a calcium/hydrogen antiporter. Strontium's ability to mimic calcium allows it to bind in place of calcium in the calcium/hydrogen antiporter. The binding of strontium reduces the efficacy of the antiporter, thereby reducing the amount of glutamic acid that can be loaded into a vesicle. As noted above, the amount of glutamic acid released correlates to the level of pain/itch perceived on a log based scale. Accordingly, small changes in the amount released translate into large changes in the perception of pain/itch. Reducing the amount of glutamic acid packaged into the vesicles translates into a reduced amount of glutamic acid released, which further translates into a reduced perception of pain/itch.

As mentioned above, the binding of substance P to the NK1 receptor induces endocytosis of the bound receptor along with other signaling molecules. Final formation of the vesicle involves dynamin, which spirals around the neck of the endocytotic vesicle and tightens until the vesicle is released from the membrane. Dynamin is a phosphoprotein and GTPase enzyme. The calcium influx that occurs upon TCN activation results in the dephosphorylation of dynamin and its relocation from the cytosol to the membrane. The dephosphorylation of dynamin may occur though the calcium-dependent phosphatase, calcineurin. The GTPase activity generates the energy necessary to drive the tightening mechanism. Strontium's ability to mimic calcium allows it to bind in place of calcium thus blocking or reducing the effectiveness of dynamin 1.

As mentioned above, the mitogen activated protein kinases (MAPK) are involved in directing cellular responses to a diverse array of stimuli, such as mitogens, osmotic stress, heat shock and inflammation. The MAPK family consists of three major members: extracellular signal-regulated kinases 1 and 2 (ERK-1/2), p38, and c-Jun N-terminal kinase (JNK), which represent three separate signaling pathways. Accumulating evidence shows that all three MAPK pathways can contribute to pain sensitization after tissue and nerve injury via distinct molecular and cellular mechanisms. Activation of ERK-1/2, p38, and JNK leads to the synthesis of proinflammatory and/or pronociceptive mediators, which can result in enhanced and prolonged pain. MAPKs can be activated at either the cell membrane or in the cytosol. Once activated, MAPKs can phosphorylate proteins in both the cytosol and nucleus. Thus, MAPKs can relay extracellular stimuli from the plasma membrane to cellular targets distant from the membrane, such as transcription factors, initiating diverse cellular responses. In some pathways, it is believed that activated MAPKs undergo endocytosis to allow rapid transport to remote locations (e.g. nuclease) to facilitate the propagation of signals to remote cellular locations. Accordingly, strontium's ability to block endocytosis can prevent MAPKs from activating downstream targets.

F. Strontium Blocks Exocytosis of Substance P From Dense Core Granules

Two main neurotransmitters involved in TCN transmission are glutamic acid and substance P. Glutamic acid and substance P are packaged in vesicles and are released from presynaptic vesicles by exocytosis. As mentioned above, glutamic acid is released with low frequency nerve activation whereas substance P is only released with high frequency nerve activation.

Neurotransmitters are stored in vesicles at the end of a neuron and are held in place by calcium sensitive vesicle membrane proteins (VAMPs). The influx of calcium into the neuron terminal triggers the release the neurotransmitter vesicle. Once released, the vesicle travels to the presynaptic membrane. Fusion of the vesicle is dependent on a second wave of calcium ions, which bind to synaptotagmin. Synaptotagim works with soluble NSF attachment protein receptor (SNARE) to affect exocytosis of the vesicle and release of the neurotransmitters. Strontium reduces or blocks the exocytosis of neurotransmitter vesicles by binding to the calcium receptor on synaptotagmin.

G. Limitations of Strontium on Nociception and Inflammatory Pathways

It has been surprisingly discovered that the reason strontium is frequently unable to completely block pain, itching or inflammation is due to two factors: (1) the limited amount of strontium that can be topically applied, after which the hyperosmotic effects of the strontium salts themselves start to cause pain, itching or inflammation; and (2) the ability of strontium to stimulate pathways that may act to negate strontium's inherent anti-irritant activities, thus reducing the overall therapeutic benefit.

Regarding the first factor, this is due to the fact that strontium has a relatively low potency in its ability to suppress pain, itching and inflammation compared to many other drugs with similar therapeutic goals (e.g. non-steroidal anti-inflammatory drugs). It is this low potency of strontium that prevents it from blocking pain when it is orally ingested in the form of the prescription drug, strontium ranelate that is approved for treatment of osteoporosis in over 100 countries. Regarding the second factor, the degree to which strontium will negate its anti-irritant benefits depends on many factors related to the type of nerve damage that caused the neuropathic condition to develop (e.g., viral infection, physical trauma such as amputation or nerve compression, metabolic nerve damage as occurs in diabetes, coexisting inflammation and other factors.

Beta Hydroxybutyrate Affects Nociception and Inflammation Pathways

Beta hydroxybutyrate, (also known as beta hydroxybutyric acid, beta hydroxybutanoic acid, 3-hydroxybutyrate, 3-hydroxybutyric acid, 3-hydroxybutanoic acid, D-3-hydroxybutyrate, R(3-hydroxybutyric acid), D,R (racemic mixture of D and D), and natural form and collectively referred to as "BHB") is a beta hydroxy acid. BHB acts at different steps in the same inflammatory pathways inhibited by strontium, and thus in effect amplify the basic anti-irritant and anti-pain activity and nociceptor-protective activities of strontium. The effects of BHBs on some of the key nociception and inflammatory pathways are discussed below.

A. G Protein-Coupled Receptor A

G protein-coupled receptor 109A (GPR109A) is a receptor for nicotinic acid, also known as niacin or vitamin B3 (collectively referred to as "niacin"). High doses of niacin are commonly used to treat high cholesterol levels in humans One unpleasant side effect of high doses of niacin is flushing/blushing, which is a reddening of the skin due to vascular dilation often accompanied by an itching or burning sensation. Flushing/blushing occurs due to the activation of GRP109A with the binding of niacin. Activation of GPR109A increases cyclic AMP (cAMP) levels and releases arachidonic acid from cell membranes. Arachidonic acid is metabolized to produce prostaglandins (including D2 and E2), prostacyclin, and thromboxane. Activation of the prostaglandin D2 and E2 receptors, EP4, and IP receptors can lead to vasodilation of the blood vessels resulting in flush/blush of the skin.

BHB also binds to GPR109A. The present disclosure includes the unexpected finding that BHB does not activate the flush/blush response like niacin.

B. BHB Inhibits Presynaptic Vesicle Loading

Similar to strontium, BHB also affects the vesicular filling of glutamic acid (VGLUT2) and ATP (VNUT). However, BHB uses a different mechanism than strontium. As discussed above, the loading of vesicles uses a hydrogen gradient that is created by a calcium/hydrogen antiporter. The calcium/hydrogen antiporter has a unique regulatory system that requires the presence of chloride in order to work. BHB blocks the chloride binding site, thus reducing the efficacy or even shutting down the calcium/hydrogen antiporter.

C. Mast Cell Degranulation

Mast cells are part of the immune system and contain granules packed with histamine, heparin, proteoglycans, serotonin and proteases. Mast cell can be activated by many different mechanisms. Once activated, mast cells rapidly degranulate to release the granule contents, which activate various inflammatory pathways.

Polyhydroxyphenols Affect Nociception and Inflammation Pathways

Polyhydroxyphenols are phenolic compounds possessing at least two hydroxyl groups. In one embodiment, the polyhydroxyphenols also exhibit one or more carboxyl groups. Also contemplated by the present disclosure are polymeric phenolic compounds that have two or more aromatic rings that typically, but do not necessarily have the same structure.

Polyhydroxyphenols act at different steps in the same inflammatory pathways inhibited by strontium, and thus in effect amplify the basic anti-irritant and anti-pain activity and nociceptor-protective activities of strontium. The effects of polyhydroxyphenols on some of the key nociception and inflammatory pathways are discussed below.

A. Polyhydroxyphenols Inhibit Multiple Inflammatory Pathways That Activate Nociceptors Polyhydroxyphenols are powerful antioxidants that directly bind to components of NF-Kappa B and cause a direct inhibition of activation. They also directly inactivate superoxide, hydrogen peroxide, hydroxyl radicals and hypochlorous acid, thus preventing them from shifting the intracellular GSH concentration from being reduced, which activates NF-Kappa B and other redox activated inflammatory regulatory molecules and molecules that directly activate nociceptors. Polyhydroxyphenols also inhibit the expression of multiple cellular adhesion molecules like ICAM-1, VCAM-1 and members of the Selectin adhesion molecules that enable neutrophils and monocytes to extravasate from blood vessels and accumulate at sites of inflammation, thus contributing to nociceptor activation.

Polyhydroxyphenols are also inhibitors of protein kinase C (PKC) isozymes, and in particular, PKC epsilon. (See, for example, Cancer Res. 70(6): 2415-2423 (2010); and Biochem. Pharmacol. 38: 1627-1634 (1989), both incorporated by reference herein.) Also as described and demonstrated by both of these articles, methods for determining the degree of inhibition of PKC by compounds are known in the pharmaceutical arts. This is particularly useful since strontium can mimic the effects of calcium as a cofactor for PKC. As used herein, the polyhydroxyphenol will be considered to be a PKC inhibitor if it suppresses 10% or more of the activity of the PKC.

Polyhydroxyphenols are also known inhibitors of calmodulin. More particularly, they inhibit calmodulin-promoted phosphodiesterase activity. See, for example, Plant and Cell Physiol. 26(1) 201-209 (1985), which describes inhibition of calmodulin-promoted phosphodiesterase activity by flavonoids such as catechin, epicatechin, quercetin, caffeic acid and naringenin. As used herein the polyhydroxyphenol will be considered to be a calmodulin inhibitor if it suppresses 10% or more of the activity of calmodulin Polyhydroxyphenols are also known as adenosine triphosphate (ATP) analogues.

ATP is a molecule that binds to the active sites of kinases like protein kinase C and other regulator kinases that are part of signal transduction pathways that active multiple inflammatory pathways, activate NF-Kappa B and directly activate nociceptors. These kinases are also known to be necessary for development of neuropathic nociceptor sensitization and neuropathic pain and pruritus. Polyhydroxyphenols that have hydroxyl groups adjacent to each other on the phenolic moiety in meta and para positions mimic the three dimensional structure of ATP and compete with ATP for the protein kinase ATP binding site. Binding of the polyhydroxyphenol to the ATP binding site prevents protein kinase from being active. Studies of the activities of various ATP analogues, such as flavonoids, are known in the literature. (See, for example, Phytochemistry Reviews 1:325-332 (2002), wherein the effect of flavonols on ATP-dependent activities was studies, incorporated by reference herein.)

Polyhydroxyphenols also possess an ability to inhibit the Fenton Reaction by which low concentrations of ferrous iron ($Fe_2^{++}$) and copper ($Cu^{++}$) catalytically produce the highly toxic and inflammatory hydroxyl radical that is a powerful inflammation activator.

Polyhydroxyphenols additionally are powerful inhibitors of prostaglandins and leukotrienes, particularly PGE2 and LTB4. PGE2 is one of the most important nociceptor sensitizers that is synthesized in virtually all inflammatory conditions. LTB4 is one of the most important attractants and activators of neutrophils that are the first cell to accumulate in large numbers at sites of trauma, irritation, infection and inflammation and are among the most important triggers of nociceptor activation.

Polyhydroxyphenols also have powerful inhibitory activities on one of the most important inflammatory molecules, the mast cell. Mast cells are present in the dermis and submucosal tissues throughout the body and are among the most important sources of preformed inflammatory mediators like histamine, TNF-alpha, IL-1, and IL-6. Nociceptors are activated, either directly or indirectly, by TNF-alpha, IL-1, IL-6 and others. Nociceptor activation is also a major stimulator of substance P release from TCN that directly activates mast cells, neutrophils and every other type of inflammatory white blood cell.

Furthermore, polyhydroxyphenols also have a critical ability to inhibit several inflammatory and nociceptor activating pathways that are stimulated by strontium. In particular, strontium's ability to activate the calcium-sensitive receptor (CaSR) on cells, including nociceptors is known to activate protein kinase A, protein kinase C and NF-Kappa B. Activation of each of these molecules is known to contribute to nociceptor activation and neuropathy development. Combining strontium with polyhydroxyphenols would limit such activation, thus negating the undesirable activities of strontium.

Polyhydroxyphenols also have the ability to alter the intracellular calcium dynamics Specifically, they reduce the increase of intracellular calcium in response to pain and inflammation-triggering extracellular stimuli.

Combining strontium with the polyhydroxyphenols as described herein, results in complexes that are more efficient inhibitors of many of the same nociceptor-activating pathways that are inhibited by strontium alone by having multiple, overlapping and distinct mechanisms. Additionally, polyhydroxyphenols also inhibit strontium-activated pathways that contribute to pain, pruritus and development of neuropathic diseases.

B. Polyhydroxyphenols Bind to Conserved Hydrophobic Sites

Polyhydroxyphenols are known to bind to hydrophobic amino acids like phenylalanine, tyrosine and tryptophan via pi-pi bond stacking. The hydroxy groups are also important since they can hydrogen bond to the amide and carbonyl groups of a peptide backbone in a protein and to select amino acid side chains. Among amino acids to which gallic acid and other polyhydroxyphenols bind, proline and other aromatic amino acids are among the most important.

Cysteine Based Antioxidants Affect Nociception and Inflammation Pathways

Cysteine is abbreviated by the three letter amino acid code, Cys. Cysteine is a naturally occurring amino acid that is present in many foods and proteins. Cysteine has a thiol side chain, which is easily oxidized. Because of its high reactivity, the thiol group of cysteine has numerous biological functions. In a broad sense, cysteine possesses the following broad pharmacological activities: (1) antioxidant activity, (2) direct regulation of redox-sensitive regulatory molecules, and (3) inhibition of intracellular calcium levels that triggering pain and inflammation, each of which is discussed below.

A. Cysteine, Cystine, and Glutathione

Cystine is amino acid compound made up of two cysteine molecules bound together by a single disulfide bond. In the extracellular environment, cystine is the predominant form and is the only form transported into cells by a specific amino acid exchanging molecule, the System $X_C^-$ antiporter. This protein exchanges extracellular cystine for intracellular glutamic acid using the relative concentration gradient between the two as the source of transport energy. Within cells, the disulfide bond of cystine is reduced to form two molecules of cysteine, each possessing a free sulfhydryl group. Free cysteine is then incorporated into the tripeptide, glutathione, gamma-Glu-Cys-Gly. Glutathione is the most prevalent and important intracellular thiol anti-oxidant in all cells and acts as a reduction/oxidation 'redox' switch that directly or indirectly controls the expression of hundreds of regulatory molecules, many of which are potent pain and inflammation inducers. Free cysteine can also directly inactivate reactive oxygen species (ROS) that can inactivate regulatory proteins and, oxidize lipids and directly cause mutations in DNA that can lead to abnormal cellular growth and cancer.

Cysteine is the rate-limiting amino acid that controls the synthesis of reduced glutathione (GSH). Accordingly, administration of a cysteine based antioxidant increases the concentration of GSH and reduces the intracellular concentration of oxidized glutathione (GSSG), thus normalizing a nociceptor's redox state. This has the immediate effect of inhibiting the activation of NF-Kappa B and the activation of many other redox-sensitive inflammatory pathways, thus reducing nociceptor activation by both direct and indirect pathways. Cysteine based antioxidants also have a unique antioxidant activity due to their thiol (SH groups) that suppress the ability of nitric oxide to covalently bond to and activate inflammatory kinases that are known to directly contribute to neuropathic conditions. Cysteine based antioxidants also directly inactivate other oxidants that activate inflammatory pathways and, most importantly, they inhibit nociceptor activation.

B. Cysteine Based Antioxidants Inhibit Multiple Strontium Regulated Inflammatory Pathways That Activate Nociceptors Due to its thiol group, cysteine based antioxidants also have the ability to directly bind to the thiol groups of cysteine residues within molecules that are part of inflammatory pathways that contribute to nociceptor activation. Since there are many thiol-sensitive regulatory molecules, cysteine-based anti-oxidants have the ability to block oxidation of critical cysteines in such molecules and thus block activation that leads to increased inflammation and nociceptor activation. For many redox sensitive cysteine regulated pathways, the concentration of calcium within nociceptors is increased and, as for many other nociceptor activators, the resultant calcium-concentration encoded pain, pruritus and activation signals contribute to the formation and the long-term continuation of neuropathic conditions.

One particularly important thiol-sensitive pain- and inflammation-inducing molecule present on nociceptors and inflammatory cells is the transient receptor potential ankyrin, subtype 1 (TRPA1) that is highly sensitive to oxidation of its free cysteine amino acids that trigger pain, itch and inflammatory responses. TRPA1 is unique among the known oxidation-sensitive ion channels in its sensitivity to a wide range of chemical irritants found in the environment, inflammatory chemicals released in inflammatory reactions like hydrogen peroxide and prostaglandin metabolites and chemicals in spicy, pungent foods. It is considered to be one of the most important "chemosensors" present on nociceptive neurons, immune cells and epithelial cells. Simple thiol anti-oxidants, like those in the present disclosure, can prevent or reverse oxidation of cysteines in TRPA1 and can thus prevent its activation and generation of pain and inflammatory responses due to irritant chemicals in the stomach contents and inflammatory reactions in the esophageal mucosa.

Cysteine based antioxidants also have the ability to alter the intracellular calcium dynamics Specifically, they reduce oxidized regulatory proteins that regulate intracellular calcium levels. When cells are exposed to inflammatory mediators, reactive oxygen species oxidize molecules in the endoplasmic reticulum that stores calcium and releases it into the cytoplasm in response to an initial calcium-mediated signal. These oxidized molecules increase the sensitivity of the calcium release mechanism and increases the magnitude of the signal, thus potentially increasing both pain and inflammatory responses.

C Limitations of Cysteine Based Antioxidants on Nociception and Inflammatory Pathways In certain situations cysteine base antioxidants can cause more harm than benefit. It is believed that in low pH (e.g. acidic conditions) and high osmolarity (e.g. high cysteine based antioxidant concentrations) situations, the presence of cysteine based antioxidants will increase damage in tissue rather than decrease. Each is discussed briefly below.

Acidic conditions can induce pain via activation of acid sensitive ion channels, the most notable being acid sensing ion channels (ASICs) and the Transient receptor potential vanilloid 1 (TRPV1). ASICs are a family of voltage insensitive cation channels that are activated in the presence of excess hydrogen ions (i.e. acidic environments). All ASICs are present in the peripheral nervous system with ASIC3 specifically expressed in nociceptors.

Activation of ASICs leads to the perception of pain. TRPV1, also known as the capsaicin receptor and the vanilloid receptor 1, can be activated by a wide variety of exogenous and endogenous physical and chemical stimuli such as high temperatures, acidic conditions, capsaicin, and allyl isothiocyanate. TRPV1 is a central integrator of pain, itch, and inflammation. Activation of TRPV1 directly sensitized other molecules such as the opening of calcium ion channels and the release of substance P, resulting in a painful burning sensation.

It is believed that some reducing agents (e.g. antioxidants, cysteine based antioxidants) can also activate ASICs. Additionally, cysteine based antioxidants can also activate calcium ion channels and thus acts synergistically with ASIC1a and TRPV1 to intensify the perception of pain, itch, and inflammation.

It is believed that molecules with free thiol (—SH) groups can activate and open ion channels on nociceptors, resulting in the transmission of pain, itch, and inflammation signals. Furthermore, this activation occurs at low millimolar to micromolar concentrations. Additionally, release of cysteine from the cytoplasm triggers nociceptor activation. Based on the above, compositions and formulations containing high concentrations of cysteine based antioxidants can (1) activate nociceptors and (2) mimic high extracellular cysteine levels that also activate nociception.

Unexpectedly, it has been found that by combining cysteine based antioxidants with strontium, even at low pH or high concentrations of cysteine based antioxidant actually reduces pain, itch, and inflammation. Without wishing to be bound by any one theory, it is believed that opening ion channels in the presence of strontium, allows greater levels of strontium to enter the nociceptor and shut down or decrease its activity. This is due to (1) strontium having a higher affinity than calcium for flowing into the ion channels and (2) the excessive amount of strontium ions present as compared to the physiological levels of calcium present.

Furthermore, cysteine based antioxidants and strontium target different mechanisms to block nociception. The combination results in a synergistic affect
that provides a surprising level of pain, itch, and inflammation relief as compared to the individual compounds.

Psoriasis

Psoriasis is an immune-mediated skin condition characterized by lesions. There are five main types of psoriasis, plaque, guttate, inverse, pustular, and erythrodermic, of which, plaque is the most common. The skin lesions associated with psoriasis are generally due to the abnormally excessive and rapid growth of skin cells, resulting in buildup and thick patches referred to as plaques. The skin cells are replaced every 3-5 days instead of the usual 28-30 days. The rapid skin growth is maintained through a vicious cycle of the inflammatory system triggering cell growth, which in turn triggers the inflammatory system.

It is believed that the psoriatic cycle begins with a triggering event such as trauma, infection, or stress that causes the keratinocytes to become stressed and activates dendritic cells. The dendritic cells release IL-12 and IL-23, which in turn stimulate Th17 and Th1 cells respectively. Th17 releases TNF-alpha interferon-gamma which stimulates inflammation. Similarly, Th1 cells release IL-17 which stimulates inflammation. Th1 cells also stimulate keratinocyte division leading to the formation of plaques. The activation of immune cells releases cytokines which also activates keratinocytes. The interaction between the immune system and keratinocyte activation becomes a self-feeding cycle.

Preliminary investigations indicate that strontium can break up the inflammatory/keratinocyte cycle of psoriasis, specifically by blocking the IL-17 and TNF-alpha. By targeting and blocking the two main pathways that activated dendritic cells use to trigger a psoriatic episode, strontium has immense potential as a therapeutic for psoriasis.

Atopic Dermatitis

Atopic dermatitis, also referred to as eczema is a condition that present as dry, itchy, inflamed skin. The condition can also manifest as raised lesions that weep, crack, swell, and crust over. The lesions present an increased risk for bacterial, fungal, or viral infections. While the cause of atopic dermatitis is unknown, it is believed that many factors contribute to the conditions including, but not limited to, genetics, microbes, and environmental.

It is believed that people with atopic dermatitis have higher levels of *Staphylococcus aureus* on their skin. The higher bacterial levels trigger an immune response via the toll-like receptors, in particular toll-like receptor 4 (TLR-4). It is also believed that continual activation of TLR-4 contributes to the chronic nature of atopic dermatitis.

Other molecular pathways activate in atopic dermatitis include matrix metalloproteinases (MMPs). MMPs are a family of enzymes capable of breaking down extracellular matrix proteins, including connective tissues.

Preliminary data indicate that strontium can block the TLR-4 and MMP activity.

Herpesviridae, Shingles, and Post Herpetic Neuralgia

Herpesviridae is a large family of viruses that cause disease in people and animals. The family includes herpes simples virus 1 and 2 (HSV1, HSV2), varicella zoster virus, Epstein-Barr virus, cytomegalovirus, roseolovirus, and Kaposi's sarcoma-associated herpesvirus. After the initial infection resolves, many of the herpes viruses remain latent in the nerve cell bodies. The virus can be reactivated days, months, years, or even decades later. Upon activation, the virus travels down the nerve axons to cause viral infection of the skin (e.g. blistering rash) in the region of the nerve.

Herpes Simplex causes several distinct medical disorders based on the site of infection. Common infection sites include the face/mouth (orofacial herpes), anogenital (genitalia herpes), hands (herpetic whitlow), eyes (herpes keratitis), and central nervous system (herpes encephalitis). HSV1 and 2 generally present as painful and/or itchy small red bumps that develop into fluid filled blisters. The blisters rupture leaving behind an ulcer that scabs over and eventually heals. Treatments range from antivirals to analgesics to dietary supplements.

Varicella zoster virus (VZV) initially presents as chicken pox in children. Once the initial infection has resolve, the virus can remain inactive for decades. Activation of the virus results in a condition commonly referred to as shingles or zoster. Shingles initially presents with flu-like symptoms such as headache, fever, and malaise followed by burning pain and itching sensations. A rash generally develops with one to two days of the initial symptoms but could be as long as three weeks later. The rash presents as red, fluid filled blisters that break open and crust over. The rash typically appears on one side of the body in a belt-like pattern. The rash generally heals within two to four weeks. In older adults, the rash can be more severe and last longer.

Post herpetic neuralgia (PHN) is a conditions where the patient experiences continued pain for months or years after the rash has resolved. PHN occurs in about 2-20% of shingles patients. The pain typically occurs in the same area affected by shingles, can be intermittent or constant, and can mimic the broad spectrum of pain sensations associated with shingles. PHN can result in increased sensitization of the skin, a condition referred to as allydynia. The actual cause of PHN is unknown; however, it is believed to be due to inflammation or damage to the affected nerve. Post herpetic neuralgia is extremely difficult to treat and treatments range from antivirals to analgesics to antidepressants and anticonvulsants.

Preliminary investigations indicate that strontium can reduce and or eliminate the pain, itch, and rash/blister formation associated with HSV1. Without wishing to be bound by any one theory, it is believed that strontium's ability to block NF-Kappa B contributes to minimizing the symptoms associated with an active infection. As mentioned above, HSV 1 and 2 require the activation of NF-Kappa B for de novo virus synthesis. By blocking NF-Kappa B, strontium is essentially stopping the infection at an early stage.

Preliminary investigations indicate that strontium can reduce or block the pain associated with PHN.

Wound Management

The skin provides a protective barrier against microbial infection. Damage to the skin presents opportunities for microbial infection. Accordingly, controlling infection is an important aspect of wound management. In most cases, e.g. minor cuts, infection is a minor consideration. However, when damage occurs on large areas of skin (e.g. burns) or with prolonged open wounds (e.g. ulcers) controlling infection becomes crucial. Controlling infection usually occurs through the use of antimicrobials such as antibiotics and antifungals. However, prolonged use of antibiotics can lead to bacterial resistance. To date, only two antibiotics, iodine and silver, have never shown bacterial resistance. That being said, neither iodine nor silver can be used to treat a systemic infection.

A. Burns

Burns can be caused by heat, electricity, chemicals, friction, or radiation. Burns are categorized based on the depth of damage to the skin and underlying tissue. First degree or superficial burns affect only the outer layer of the skin, i.e. epidermis. Second degree or partial-thickness burns penetrate into the underlying layers of the skin, i.e. upper layers of dermis. Third degree or full thickness burns extend through all layers of the skin. Fourth degree burns involve deeper tissue such as muscle or bone. Chemical burns can be caused by any corrosive substance such as acids, bases, oxidizers, solvents, reducing agents or alkylants. Chemical burns are unusual in that the damage may not be immediately noticeable (e.g. under the skin). One notable source of chemical burns is from chemicals being used as weapons. Non-limiting examples include choking irritants, vesicants/blistering agents, blood agents, nerve agents, vomiting agents, riot control agents, incapacitating agents, toxins, and allergens.

Treatment of burns depends on the severity. Minor burns, i.e. first degree and second degree burns that are less than 2-3 inches in diameter, can generally be self-treated by keeping the area clean and taking over the counter medications for pain. Major burns, i.e., second degree burns larger than 3 inches in diameter and all third and fourth degree burns, require medical treatment. Treatment of major burns often involves the use of dressing to (1) absorb exudate, (2) maintain a high humidity at the wound site to encourage healing, and (3) reduce the risk of infection. A variety of different wound dressing are available, non-limiting examples include hydrocolloid, polyurethane film, hydrogel, silicon coated nylon, biosynthetic skin substitute, antimicrobial (e.g. silver and iodine), fiber, and wound dressing pads. Some of the available dressings use polymers to absorb exudate and create a gel-like barrier to help keep the wound moist. Others contain antimicrobials such as silver or iodine.

The strontium base compositions and formulations disclosed herein could be beneficial for use in managing burns. Preliminary clinical evidence indicates that topically applied strontium based compositions and formulations can provide relief from pain and itch associated with minor burns such as sunburns or small sized thermal burns. Preliminary clinical evidence also indicates that when applied shortly after the incident, topically applied strontium based compositions and formulations can reduce or eliminate the formation of blisters or the skin peeling. For major burns, topically applied strontium based compositions and formulations could also be used to help manage pain, itch, and inflammation associated with major burns. For example, the strontium based compositions and formulations could be applied to the burn area before applying the dressing. Alternatively, the strontium based compositions and formulations could be integrated into or part of the wound dressing. Additionally, use of strontium based compositions and formulations disclosed herein could reduce or prevent the development of neuropathic pain or itch due to the burn. Lastly, the strontium based compositions and formulations disclosed herein could prevent or reduce the formation of scars.

B. Surgery and Trauma

Prevention of infection is also critical during and after surgery and after traumatic incidents that results in the rupture of the skin. With respect to surgery, medical personnel typically use iodine solutions to clean their hands and the surgical site. Post-surgery, the incision is usually coated with antibacterial and kept covered using a dressing. The strontium based compositions and formulations disclosed herein could be useful in treating post-surgical wounds and amputation stumps. Additionally, the strontium based compositions and formulations disclosed herein could be useful in treating the pain, itch, or irritation associated with post-surgical wounds and amputation stumps. Lastly, the strontium based compositions and formulations disclosed herein could prevent or reduce the formation of scars.

C. Strontium Based Compositions and Formulations

In one embodiment, the strontium based compositions and formulations for use in wound treatment further include iodine or silver to provide additional antimicrobial support.

One non-limiting example uses strontium iodide salts. Strontium iodine provides another unexpected benefit in that the color is much lighter than standard iodine. One of the downsides of iodine is that the color looks like dried blood. Accordingly, having a lighter strontium iodine composition/formulation would help medical professionals evaluate wound status. In another embodiment, the strontium iodine or strontium silver compositions and formulations can further include BHB. As noted above, BHB acts on the same or different nociception and inflammatory pathways as strontium. Accordingly, its inclusion could synergistically enhance the effects of the strontium iodine or strontium silver salts. In another embodiment, the BHB is in polymer form. The breakdown of the BHB polymer results in individual BHB molecules. Accordingly, the BHB polymer can provide extended release of BHB. In another embodiment, the strontium based compositions and formulations disclosed herein can be integrated in or part of wound dressing.

In one embodiment two separate formulations are used in tandem. The first formulation is strontium iodine or strontium silver. The second formulation is strontium and at least one beneficial agent (discussed below) such as polyhydroxyphenol, cysteine based antioxidant, or BHB. The first formulation is used when the risk of infection is high, e.g. early stage of burn management. The second formulation is used when the risk of infection is not as high, e.g. after a layer of epithelial tissue is covering the majority of the wound. The dual/tandem formulation would allow the use of oxidizing agents (e.g. iodine) and antioxidants/reducing agents (e.g. polyhydroxyphenol and cysteine based antioxidant) during key phase of the wound healing.

D. Application and Treatment

Burns, surgical incisions, and amputations tend to cause nerve damage and therefore result in neuropathic pain. One way to potentially minimize the development of neuropathic pain is though the immediate and/or continuous application of the strontium based compositions and formulations disclosed herein. This can be achieved through routine application or extended release formulas or the use of a device that continually releases the strontium based compositions and formulations. In one embodiment, treatment is continuous for the first few days or weeks. As the wound heals, treatment can be more intermittent based on the patients pain, itch, or irritation level. Ultimately, the patient's perception of pain, itch, or irritation determines the frequency of application.

Restless Leg Syndrome

Restless leg syndrome (RLS), also referred to as Willis-Ekbom disease or Wittmaack-Ekbom syndrome, is a neurological disorder which causes an uncomfortable "itchy," "pins and needles," or "creepy crawly" feeling in the legs (and sometime arms or other parts of the body). Moving the affected body part can provide temporary relief. Causes of RLS include genetic predisposition, iron imbalance (too low or too high), and certain medications.

Unexpectedly, it has been found that topically applied strontium based compositions can reduce or eliminate the symptoms associated with RLS.

Joint Pain

Joint pain has many causes including but not limited to arthritis, injury, and repetitive motion. With respect to arthritis, there are over 100 different causes of arthritis, which are roughly divided into two main categories. The first category is arthritis caused by wear and tear of the cartilage and the second category is arthritis associated with inflammation, generally associated with an overactive immune system. The most common causes of arthritis are osteoarthritis, rheumatoid arthritis, and psoriatic arthritis. Regarding injuries, the injury may be a sprain, strain, or twist that leads to damage and/or inflammation of the tendons, ligaments, or cartilage. Regarding repetitive motion injuries, the term is used to cover a range of conditions associated with repetitive tasks, forceful exertions, vibrations, mechanical compression, or sustain/awkward positions. Non-limiting examples of repetitive motion injuries include carpal tunnel syndrome, cubital tunnel syndrome, golfers elbow, tennis elbow, De Quervain syndrome, thoracic outlet syndrome, intersection syndrome, stenosing tenosynovitis, radial tunnel syndrome, and focal dystonia.

The present disclosure includes the unexpected discovery that the strontium based compounds described herein can provide relief for joint pain when topically applied.

Initial theories on joint pain and inflammation management believed that the pain reliever/anti-inflammatory needed to be at the origination of the pain/inflammation, e.g. deep within the joint. Without wishing to be bound by any one theory, it is believed that disruption of the nerve signaling on the nerve endings also disrupts the nerve signals deeper in the tissue based on the following concepts. First, physiologically a single nerve reaches from the spinal cord to just below the surface of the skin. Second, nerve signal propagation is based on the flow calcium along the nerve in a wave like fashion. And third, the intensity of the signal correlates to the frequency of the calcium wave. Based on these three concepts, disruption of the calcium wave at the end of the nerve can affect signal propagation further along the length of the nerve. The disruption in signal propagation can lead to a reduction or elimination in the perception of pain or itch.

Hyperosmotic Formulations

Recent research has demonstrated that high osmolarity formulations activate specific osmotic sensors present on nociceptors, keratinocytes and immune or inflammatory cells. An example of this is the "salt in the wound" effect that causes stinging and burning if a concentrated solution of a simple salt is poured into wound. In addition to causing discomfort, high osmolarity solutions can directly activate inflammatory cells and cause them to release chemicals that cause nociceptor activation.

A. Hyperosmotic Formulations can Also Physically Damage Tissues and Cause Pain and Inflammation Topical formulations with high osmotic activity (over 400 mOsm, such as between 400 and 2000 mOsm) may also damage delicate tissues and may cause pain, especially in non-keratinized skin that have a mucous membrane or tissue that has a damaged 'barrier function' due to physical trauma, infection or inflammation. Such hyperosmotic-induced damage is popularly known as "the salt in the wound effect" and it occurs when osmotic forces cause water to flow out of the cells and tissues into the hyperosmotic formulations. It is also believed that application of hyperosmotic formulations can directly activate certain molecules that act as osmolarity sensors and, when activated, activate pain sensing nerves and immune and non-immune cells that can produce inflammation and cellular damage. This recent understanding has potentially critical importance for the goal of preventing the development of chronic or neuropathic pain.

The potential importance of this observation has critical importance for the treatment of or the prevention of neuropathic pain development since chronic nociceptor activation is known to be required for painful neuropathic conditions to develop. The recent discovery that there are multiple ion channels and related hyperosmotic molecular sensors that trigger nociceptor activation upon exposure to hyperosmotic topical formulations suggests that their chronic use may predispose the development of neuropathic pain conditions if there is coexisting chronic or severe damage to nociceptors. In this scenario, long-term application of a hyperosmotic formulation to skin, and especially to delicate mucous membranes of, for example, the vaginal or cervical mucosa may cause low level, but long-term activation of nociceptors, thus contributing to their sensitization. It is believed that that progression of from an acute, transient pain state to a chronic, long-lasting, 'neuropathic state' is due to continued excessive nociceptor activation that results in increased expression of genes that reduce the magnitude of an irritant stimuli, also called the irritant or nociceptor activation 'threshold' and thus cause increased nociceptor activation and an increased perception of pain and/or pruritus. Additionally, these genes can also increase the synthesis of inflammation-producing molecules that further irritate the nociceptors, thus producing what is commonly termed 'a vicious spiral' of increasing sensory irritation and inflammation.

B Hyperosmotic Formulations can Also Increase Infection by Herpes & HIV

In addition to causing painful or pruritic sensations and inflammation, even low-level, but chronic exposure to nociceptor-activating irritants can predispose to infection by a multitude of pathogenic microbes of which Herpes simplex viruses 1 and 2 (HSV) and the Human Immunodeficiency Virus (HIV) cause the greatest threat to public health. While a detailed explanation of the many and varied reasons for why nociceptor activation and coexisting inflammation facilitates infection by HSV and HIV is not discussed in detail herein, in essence, the release by Type C Nociceptors of inflammatory neuropeptides like substance P is known to damage the anatomical 'barriers' of both keratinized skin and mucosal membranes that block viral infection. The resultant inflammation is also known to activate inflammatory immune cells that, ironically, contribute to the ability of both HSV and HIV to cause acute infection and in the case of HSV, reactivation of an existing latent infection.

Application of hyperosmotic topical formulations of, for example, lubricants or microbicides, to the mucous membranes of male or female genitals or to the vaginal, cervical or anal tissues may greatly increase the possibility of transferring one of these viruses or other pathogenic microbes that cause sexually-transmitted diseases from an infected person to an otherwise healthy person. It is therefore advantageous to create strontium-containing formulations with high strontium concentrations that are designed to minimize osmotic shock.

C. Strontium Suppress Damage Due to Hyperosmotic Formulations

Initially, the "salt in the wound" effect was thought to be non-specific, i.e., the release of water by the cell was due to the presence of a salt. Without wishing to be bound by any one theory, it is believed that osmotic sensors trigger nociception and inflammation in response to changes to the extracellular environment. The osmotic receptors are G-protein coupled receptors with calcium as their endogenous ligand. Accordingly, calcium acts as one of the primary regulators of osmotic stress. Intracellular calcium levels rise during hypo-osmotic and hyper-osmotic stresses. Strontium can reduce osmotic shock by binding to the calcium receptors on the osmotic sensors and thus prevent them from triggering nociception and inflammation pathways.

pH

Human skin is protected with a layer of sebum and perspiration, often referred to as the "acid mantle." The acid mantle helps protect the skin by inhibiting the growth of bacteria and fungi and reducing exposure to environmental elements such as sunlight, pollution, or chemicals. Due to the acid mantle, the average pH of human skin is about 5.5 and can vary from 4 to 7. High skin pH tends to cause dry skin, whereas low skin pH tends to cause oily skin.

Many skin conditions arise when the pH of the skin is either too high or too low. A high skin pH permits increased bacterial growth, which can lead to infections and inflammation. A low skin pH can result in irritation and redness. Several skin conditions such as eczema and Rosacea tend to be associated with skin pH that is outside of the normal range, i.e. either too acidic or too alkaline.

Most skin products are "pH balanced" to help maintain a healthy skin pH. Unexpectedly, it has been found that compositions and formulations containing strontium work better at a low pH, e.g. lower than 4, or even lower than 3. While not wishing to be bound by any one theory, it is believed that the application of a low pH formulation on the skin activates acid sensitive ion channels such as ASIC and TRPV1 resulting in the opening of ion channels on the nociceptor. The opening of the ion channels in the presence of strontium allows greater levels of strontium to enter the nociceptor and shut down or decrease it activity. This is due to (1) strontium having a higher affinity than calcium for flowing into the ion channels and (2) the excessive amount of strontium ions present as compared to the physiological levels of calcium present.

Compositions

The compositions and formulations of the present disclosure were formulated to perform one or more of the following functions: (1) inhibit acute sensory irritation (e.g., pruritus and pain), redness, swelling and inflammation (collectively defined for purposes of this description, "irritation"), (2) inhibit chronic irritation that is characteristic of and contributes to the development and maintenance of painful or pruritic neuropathic conditions, (3) inhibit neuropathic irritation that may contribute to increased nerve sensitivity or reactivity, (4) break the neuropathic positive feedback cycle that contributes to neuropathic pain or itch, (5) prevent the development of neuropathic conditions, (6) reduce the risk of tissue infection, and/or (7) promote healing in damaged epithelial tissue. At a minimum, the compositions and formulations of the present disclosure contain strontium. In some embodiments, the strontium containing compositions and formulations also contain at least one of the beneficial agents described below. In some embodiments, the combinations of strontium and at least one beneficial agent described herein achieve the above objectives by interacting on multiple different molecular pathways, thus creating a synergistic effect that greatly outperforms the actions of each component alone. In other embodiments, the strontium based compositions and formulations of the present disclosure achieve the above objectives through continuous exposure to/application of the strontium based compositions and formulations. In yet other embodiments, the compositions and formulations are tailored for a specific disease or condition to maximize the therapeutic benefit. Exemplary compositions and formulations are formulated, for example, using the various components discussed below. These examples include tripartite complexes containing at least three components, of which, one component is strontium, as well as are bipartite complexes containing at least two components, of which, one component is strontium. The components of the tripartite and bipartite complexes are discussed below.

A. Strontium

Strontium is present as a divalent cation. Strontium is designated by its commonly used atomic symbol, 'Sr' and is depicted below.

Strontium mimics the ability of calcium to pass through voltage dependent calcium channels and once inside cells, it competes with calcium for binding to calcium-dependent receptors. Calcium is thought to play a role in the pain process by regulating the release of neurotransmitters, and thus strontium's analgesic effect may be in preventing calcium's binding to nerve cells.

Strontium is available as an inorganic or organic salt which is water soluble at room temperature in the range of 1 to 100 g/l. Inorganic salts include, for example, strontium chloride, strontium sulfate, strontium carbonate, strontium nitrate, strontium hydroxide, strontium hydrosulfide, strontium oxide, strontium acetate, etc. Organic salts include, for example, negatively charged organic acid such as a mono-, di-, tri- or tetra-carboxylic acid, or an amino carboxylic acid that may have a linear or branched carbon chain of from 2 to 30 carbon atoms and one or more amino groups attached thereto. The amino carboxylic acid may be a natural or synthetic amino acid. Examples of organic strontium salts include, for example strontium glutamate, strontium aspartate, strontium malonate, strontium maleate, strontium citrate, strontium threonate, strontium lactate, strontium pyruvate, strontium ascorbate, strontium alpha-ketoglutarate or strontium succinate. Other examples of strontium salts, and methods for preparation thereof, can be found, for example, in US Patent Application Pub. No. 2010/0048697.

B. Beta Hydroxybutyrate (BHB)

The aliphatic hydroxyacid beta-hydroxybutyric acid (also known as beta-hydroxybutanoic acid, 3-hydroxybutyric acid, and 3-hydroxybutanoic acid, as well as the conjugate base form 3-hydroxybutyrate and beta hydroxybutyrate, are collectively referred to herein as "BHB") is a beta hydroxy acid. It is synthesized by the liver during fasting states in humans and is often a used as an indicator for diabetic ketoacidosis.

BHB can be a salt form or polymer form.

C. Polyhydroxyphenols

Polyhydroxyphenols are phenolic compounds possessing at least two hydroxyl groups, preferably in the ortho and para positions. One exemplary compound is 3,4,5-trihydroxy benzoic acid, also called gallic acid. The term "polyhydroxyphenol" does not include carboxylic acids, such as ranelate. Non-limiting examples of polyhydroxyphenols include: gallic acid, caffeic acid, tannic acid, epicatechin, epigallocatechin gallate, epigallocatechin, epicatechin gallate, ellagic acid, myricetin, luteolin, naringen, genistein, apagenin, nordihydroguaiaretic acid, and esters thereof.

The polyhydroxyphenol can be added to the compositions described herein in essentially purified form, or they can be added in the form of polyhydroxyphenol-containing plant extracts, such as green tea and soy extracts.

The flavonoids are polyphenolic compounds possessing 15 carbon atoms; two six-carbon benzyl rings that are usually joined together by a linear, saturated three carbon chain.

Other flavonoids may consist of two benzyl rings joined together by a third 5- or 6-carbon ring structure. Flavonoids constitute one of the most characteristic classes of compounds in higher plants. Many flavonoids are easily recognized as the pigments in flowering plants.

The monomeric phenolic compounds, e.g. gallic acid and caffeic acid, have a carboxylic acid group, which may be esterified with a sugar moiety such as glucose. In the case of gallic acid, such esterification produces glucogallin. Other organic esters may also be effective, such as the ethyl ester of gallic acid, ethyl gallate, or the propyl ester of gallic acid, propyl gallate.

Also contemplated by the present disclosure are polymeric phenolic compounds that have two or more aromatic rings that typically, but do not necessarily have the same structure. One such example is reservatrol. Another is pentagalloyl glucose, which consists of five gallic acid residues that are esterified to one glucose molecule. This molecule will be cleaved in vivo by non-specific esterases, which free the individual gallic acid residues. The use of such forms of polyhydroxyphenolic compounds has the added advantage of lowering osmotic activity, since one molecule of pentagalloyl glucose produces one unit of osmotic activity, as compared to five units of osmotic activity produced by the use of five separate molecules of gallic acid.

Tannic acid is another example of a high molecular weight gallic acid polymer in which one or more esterified gallic acid residues are esterified to a central glucose molecule.

Ellagic acid is an example of a gallic acid dimmer. While this molecule no longer possesses the gallic acid-like phenolic structure, it does maintain many of the same bioactivities of gallic acid and is thus useful in the practice of the present disclosure.

Compounds having a flavone backbone include, for example, quercetin, and epicatechin (EC) and derivatives thereof, such as epigallocatechin gallate (EGCG found in green tea), epigallocatechin (EGC) and epicatechin gallate (ECG).

Other polyhydroxyphenolic compounds include, for example, myricetin, luteolin, naringen, genistein and nordihydroguaiaretic acid (NDGA).

In one particular embodiment, the polyhydroxyphenols that are useful also exhibit one or more carboxyl groups, such as gallic acid. The carboxyl group can serve as an additional counterion, and also assist in matrix formation with an optional polyanionic polymer.

Also contemplated is a composition that incorporates a combination of strontium with a mixture of polyhydroxyphenols, for example one or more, or two or more, of the polyhydroxyphenols noted or discussed herein and above. Using more than one polyhydroxyphenol has a synergistic effect due to the differential activities of each polyhydroxyphenol. It is contemplated that this synergistic effect has enhanced efficacy in treating sensory irritation that includes but is not limited to pain, pruritus, and development of neuropathic diseases. In one embodiment, the mixture includes monophenolic and polyphenolic polyhydroxyphenols. In one embodiment, the mixture includes monophenolic and biphenolic polyhydroxyphenols. In another embodiment, the mixture includes monophenolic and triphenolic polyhydroxyphenols. In another embodiment, the mixture includes biphenolic and triphenolic polyhydroxyphenols. In another embodiment, the mixture includes monophenolic, biphenolic, and triphenolic polyhydroxyphenols. In another embodiment, the mixture includes an ATP analogue with a monophenolic, biphenolic, or triphenolic polyhydroxyphenol. In yet another embodiment the mixture of polyhydroxyphenols is gallic acid and caffeic acid. In another embodiment, the mixture of polyhydroxyphenols is myricetin and caffeic acid. In another embodiment, the mixture of polyhydroxyphenols is myricetin and gallic acid. In another embodiment, the mixture of polyhydroxyphenols is myricetin, gallic acid, and caffeic acid.

D. Cysteine Based Antioxidant

The term "cysteine-based" includes cysteine and cystine. Alternatively the cysteine-based compound is acetylated at the amino group of the cysteine to produce N-acetyl-cysteine, commonly abbreviated acetylcysteine or NAC. Non-limiting examples of cysteine based antioxidants include: cysteine, cystine, acetylcysteine, diacetylcysteine, and esters thereof.

Cysteine exists in two enantiomeric forms, designated 'L-cysteine' and 'D-cysteine', of which the L form is used in living organisms while the D form is not. While both the L and D forms are contemplated in the present disclosure, the L form of acetylcysteine is most preferred, i.e., NAC. If the D form of NAC is intended, it will be referred to as D-NAC. In addition, both L-Cys and D-Cys can form disulfide bonds between the two thiol groups to form a 'dimer', literally a pair of Cys molecules. Such disulfide bonds occur in many proteins and play a critical regulatory role in biochemical pathways due to the ease of their reversible formation by oxidative processes and dissolution by reductive processes. By convention, a disulfide-bonded dimer of cysteine is termed cystine. Thus one cysteine molecule under appropriate reducing conditions or enzymatic processing will yield two cysteine molecules. Cystine can be formed from either two L-Cys molecules, two D-Cys molecules, or one L-Cys and one D-Cys molecules. Another exemplary cysteine-based compound is N,S-diacetylcysteine. All of such variants are incorporated within the present disclosure.

E. Silver and/or Iodine

Silver and iodine are known antimicrobials for which antibiotic resistance has never developed. Non-limiting silver compounds include silver salts (e.g. silver nitrate), silver sulfadiazine, silver zeolite, silver nanoparticles, and colloidal silver.

F. Cleavable Bonds

In one embodiment, the complexes of the present disclosure utilize a cleavable bond to join the beta hydroxybutyrate and the cysteine-based compound together in the tripartite complexes. Complexes which use a cleavable bond to join the beta hydroxybutyrate and cysteine-based compound together in the tripartite complexes will be referred to as the "conjugated" form of the compounds.

As defined above, a cleavable bond is a chemical bond joining two molecules together that can later be broken, thus releasing the two molecules from each other. The present disclosure contemplates using cleavable bonds that are known in the art, examples of which include, but are not limited to peptide bonds, thioesters bonds, enzymatically cleavable bonds, disulfide bonds, pH dependent bonds, and other covalent bonds.

The use of cleavable bonds in the present disclosure may create a less active form of the compound that can be converted to an active form. The benefits of using an less active form are known in the art. For example, the less active form may be used to enhance the stability of a compound allowing for an increase the shelf-life or a greater range of storage temperatures. The less active form may also be used to ensure that the compound reaches its target destination before becoming active.

The use of cleavable bonds in the present disclosure offer other advantages that may improve the performance of the complex. For example, the conjugated form may be used to reduce the osmolarity of a chemical compound, which in the present disclosure is useful since the human body has molecular sensors that recognize changes in osmolarity and trigger pain and itch pathways. The conjugated form may also be used to change the solubility of a compound, for example, making the compound more lipophilic to allow better uptake into cells.

As described elsewhere herein, limiting the osmolarity of the present composition herein may be beneficial. Accordingly, conjugating beta hydroxybutyrate to the cysteine-based antioxidant lowers the osmolarity by approximately one third, thus enhancing efficacy. The addition of a neutral or anionic polymer reduces the osmolarity even further by allowing multiple tripartite complexes to attach to one polymer.

In one embodiment, the cleavable bond of the conjugated form of the compound is cleaved upon application of the compound to the skin. One example of this embodiment is the use of thioester to join beta hydroxybutyrate to NAC. When this compound is applied to human skin, non-specific esterases on the surface of the skin cells cleave the thioester bond.

In another embodiment, only a small percentage of the cleavable bonds of the conjugated form of the compound are cleaved upon application of the compound to the skin or thereafter, the majority of the conjugated form of the compound is taken into the cell where the cleavable bonds are cleaved. The uptake of the conjugated form of the compound allows for a greater concentration of strontium to be present within a cell than applying a strontium salt to the skin or orally ingesting strontium.

In another embodiment, the cleavable bond is cleaved upon application of a second compound containing a cleaving agent. A cleaving agent is an agent that cleaves specific chemical bonds. The second compound can be applied to the skin immediately after the application of the conjugated form of the compound or alternatively, the two compounds can be mixed together immediately before application to the skin. Examples of cleaving agents include, but are not limited to enzymes, reducing agents, oxidizing agents, light, and chemicals that induce pH changes.

In one embodiment, the complexes of the present disclosure are derived from: 1) one atom of strontium; 2) one moiety of beta hydroxybutyrate; and 3) one molecule of N-Acetyl-L-Cysteine, (NAC) or 1) one atom of strontium; 2) two moieties of beta hydroxybutyrate; and 3) two molecules of N-Acetyl-L-Cysteine (NAC). In another embodiment, the beta hydroxybutyrate and NAC are joined by a thioester and complexed with beta hydroxybutyrate.

G. Additional Beneficial Agents

Beneficial agents synergistically enhance the effects of strontium by targeting separate molecular pathways and/or by targeting different points along the same molecular pathways. Beneficial agents may also target microorganisms that cause or contribute to conditions resulting in pain, pruritus, or irritation. Lastly, beneficial agents may also enhance strontium through unique formulations that allow for greater delivery or extended release. Any of the below listed beneficial agents may be used alone or in combination with each other.

1. Aluminum Acetate

Aluminum acetate is recognized for treating minor skin minor irritation due to poison ivy/oak, contact dermatitis, athlete's foot, etc. It is the active component in Burrow's solution.

2. Aspartame

Aspartame is an artificial sweetener. It is a methyl ester of aspartic acid and phenylalanine dipeptides. Aspartame can be used topically to treat skin irritation.

3. Colloidal Oatmeal

Colloidal oatmeal is finely ground powder from de-hulled oat seed from the *Avena sativa* plant. Colloidal oatmeal has many compounds that are beneficial for skin. Beneficial properties of colloidal oatmeal include anti-itch, anti-inflammatory, moisture retention, and antioxidant capabilities.

4. Corticosteroids

Corticosteroids are a class of molecules that are produced in the adrenal cortex. They are involved in a wide range of physiological process including stress response, immune response, and inflammation. Topical forms of corticosteroids have anti-inflammatory properties and are commonly used for the treatment or rashes, eczema, dermatitis, psoriasis, and other skin conditions. Topical corticosteroids are generally used for short periods of time as long term use can lead to secondary bacterial or fungal infection, skin atrophy, telangiectasia, bruising, and skin fragility. Non-limiting examples of topical corticosteroids include alclometasone dipropionate, amcinonide, betamethasone dipropionate, clobetasol propionate, desonide, desoximetasone, diflorasone diacetate, fluocinolone acetonide, fluocinonide, flurandrenolide, fluticasone propionate, halcinonide, halobetasol propionate, halometasone, hydrocortisone, hydrocortisone butyrate, hydrocortisone valerate, mometasone furoate, prednisone, and triamcinolone acetonide.

5. Coal Tar

Coal tar (also known as liquor carbonis detergens) is a mixture of organic compounds including phenols, heterocyclic oxygens, hydrocarbon, sulfurs, and nitrogen. Coal tar may have anti-proliferative and anti-inflammatory effects on the skin.

6. Antidepressants

Some antidepressant can have antihistamine effects and can be used to treat itching. Non-limiting examples include amitriptyline, paroxetine, doxepin, hydroxyzine, and mirtazapine. Doxepin is a tricyclic antidepressant and anxiolytic (anti-anxiety) drug that reduces reuptake of norepinephrine and serotonin (neurotransmitters) to bring their levels back to normal. Doxepin is an anticholinergic, a drug that blocks the parasympathetic nerves, and a sedative. It is the only tricyclic antidepressant to relieve itching as well as several types of pain. Mirtazapine is a noradrenergic and specific serotonergic antidepressant. It is also a histamine H1 receptor antagonist.

7. Antimicrobials

In many cases, the presence of bacteria, fungi, or viruses cause or worsen the symptoms associated with a skin disorder. For examples, high levels of *Staphylococcus aureus* are said to contribute to atopic dermatitis. Additionally, various *Candida* species worsen rashes due to excessive wet skin in infants and toddlers. Lastly, various herpes viruses cause painful blistering rashes. The antimicrobials act synergistically with strontium to promote pain and itch relief and decrease healing time. Non-limiting examples of antimicrobials include antibacterial, antifungals, or antivirals. Non-limiting examples of antibacterials include: silver, iodine, bacitracin, polymixin B, neomycin, gentamicin, mupirocin, sulfacetamide, erythromycin, neomycin, and honey. Non-limiting examples of antifungals include: benzoic acid, undecylenic alkanolamide, ciclopirox olamine polyenes, nystatin, imidazoles, bifonazole, clotrimazole, econazole, ketoconazole, miconazole, tioconazole, allylamine, terbinafine, thiocarbamates, tolciclate, tolnaftate, azoles, sulconazole, efinaconazole, luliconazole, naftifine, benzoxaborole, tavaborole and other drugs in the same class as those listed. Non-limiting examples of antivirals include acyclovir famciclovir penciclovir valacyclovir, docosanol, and lysine.

8. Plants Extracts

Many plants, herbs, and spices have anti-inflammatory, antiseptic, healing, and/or soothing properties. Non-limiting examples include jewelweed, black current seed oil, ginger, tea tree oil, mint, thyme, menthol, camphor, chamomile, comfrey (allotonin), lavender, aloe, feverfew, soy, red hogweed (*Boerhavia diffusa*), marigold (*Calendula officinalis*), licorice, white willow bark, honey, green tea, frankincense, witch hazel, cloves, *Arnica montana*, and basil.

9. Antihistamine

Antihistamines are drugs that are used to prevent the symptoms of an allergic reaction. They work by blocking histamine receptors. There are four histamine receptors, H1, H2, H3, and H4. Activation of the H1 receptors causes vasodilation and increased cell permeability. Activation of the H2 receptors stimulates gastric acid secretion. H3 receptors function as presynaptic autoreceptors on histamine-containing neurons. H4 receptors regulate neutrophil release from the bone marrow and are involved in mast cell chemotaxis. Common over the counter H1 antihistamines include diphenhydramine (Benadryl), fexofenadine (Allegra), and Loratadine (Claritin). Common H2 antihistamines include cimetidine (Tagament), Famotidine (Pepcid), and Ranitidine (Zantac). Non limiting examples of H1 antihistamines include acrivastine, azelastine, bilastine, brompheniramine, buclizine, bromodiphenhydramine, carbinoxamine, cetirizine, chlorpromazine, cyclizine, chlorpheniramine, chlorodiphenhydramine, clemastine, cyproheptadine, desloratadine, dexbrompheniramine, dexchlorpheniramine, dimenhydrinate, dimetindene, diphenhydramine, doxylamine, ebastine, embramine, fexofenadine, hydroxyzine, levocetirizine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine. Non Limiting examples of H2 antihistamines include cimetidine, famotidine, lafutidine, nizatidine, ranitidine, roxatidine, and tiotidine.

10. Local Anesthetics

Topical anesthetics are agents that reduce the sensation in the area they are applied. Non-limiting examples include benzocaine, butamben, dibucaine, lidocaine, oxybuprocaine, pramoxine, proparacaine, proxymetacaine, and tetracaine.

11. Vitamins

Topically applied vitamins have shown some promise in treating pain and itch.

Non-limiting examples include vitamin B, vitamin B12, vitamin B3, vitamin C, vitamin D, vitamin D3, vitamin E, vitamin K and other compounds that have vitamin activity such as tocopherol and ascorbic acid.

12. Moisturizers/Skin Protectants

Moisturizers/skin protectants (generally referred to as moisturizers) can be used to help maintain the integrity of the epidermal barrier and promote its protective function against dehydration, irritants, allergens, and infectious pathogens, all of which may cause itch and/or pain. Non-limiting examples include lipids, fats, oils, waxes, humectants, glycerol, honey, shea butter, lanolin, hyaluronic acid, silicone-based, allantoin, dimethicone, and ceramides.

Ceramides are a family of waxy lipid molecules that are found in high concentrations within the cell membrane of cells.

13. Over the Counter Active Ingredients, Dietary Supplements, and Homeopathic Ingredients Also contemplated are various over the counter ingredients that are beneficial for epithelial surfaces (e.g. skin or mucous membranes) as recognized by the FDA or as used by the general public. Also contemplated are various over the counter ingredients that are protective for epithelial surfaces as recognized by the FDA or as used by the general public. Also contemplated are various homeopathic ingredients that are beneficial for the epithelial surfaces. Also contemplated are various dietary supplements that are beneficial for the epithelial surfaces. Non-limiting examples of the aforementioned categories include sunscreen (non-limiting examples include zinc oxide, titanium dioxide, p-aminobenzoic acid, padimate O, phenylbenzimidazole sulfonic acid, cinoxate, dioxybenzone, oxybenzone, avobenzone, homosalate, menthyl anthranilate, octorylene, octylmethoxycinnamate, octyl salicylate, sulisobenzone, trolamine salicylate, and ecamsule), insect repellent (non-limiting examples include N,N-diethyl-m-toluamide, citronella oil, p-menthane-3,8-diol, icaridin, neem oil, dimethyl carbate, (3-[N-Butyl-N-acetyl]-aminopropionic acid, ethyl ester), dimethyl phthalate, and SS220), urea, lysine, hydroxy acids, alum, essential oils, olive oil, almond oil, coconut oil, and honey.

14. Biologics

The strontium based compositions disclosed herein can also include biologics.

Biologics are complex mixtures that are not easily identified or characterized. They can be composed of sugars, proteins, nucleic acids, or combination of the aforementioned or even living entities (e.g. cells, tissues, microorganisms). Biologics can be purified from natural sources or produced using recombinant technology. Non-limiting examples include thymus polypeptides, collazin, peptides, and tissue extracts.

15. Polymers

The strontium based compositions disclosed herein can also include polymers. Strontium and other compounds may be capable of ionic association with the polymer, thus forming a matrix. Matrix formation may enhance the bio-availability of the complexes and therefore prolongs the therapeutic effect of the composition (e.g. sustained release). The use of polymers may also minimize osmolarity. As previously mentioned, high osmolarity can lead to unstable formulations and physically damage tissues and cause pain, especially in non-keratinized skin that has a mucous membrane or a damaged "barrier function" due to physical trauma, infection or inflammation. Non-limiting examples of polymers include polyvinylpyrrolidone (PVP), dextrins, cyclodextrins, carragenans, iota carrageenan, alginic acid, xanthan gum, guar gum, sulfated polysaccharides such as carrageenan, dextran sulfate, pentosan polysulfate, condroitin sulfate, aqueous polymers, fatty acids, heparin sulfate and polyethylene glycol (PEG).

a. Alginic Acid

Alginic acid is naturally-occurring polysaccharide obtained from brown seaweed.

Structurally, it is a polyanionic linear copolymer of (1-4)-linked beta-D-mannuronic acid and alpha-L-glucuronic acid. Due to its repeated carboxyl groups, alginic acid electrostatically binds to positively charged atoms, such as strontium and calcium, when the pH of the vehicle is above the pKa of the carboxyl groups (approximately 3-4) causing them to be negatively charged and able to bind to strontium and calcium. As the pH is decreased and approaches the pH of an empty stomach (1 or less), hydrogen ions will compete with strontium and calcium and will displace and free strontium and calcium. Alginic acid thus acts as a typical ion exchange column matrix. By using various mixtures of naturally occurring alginic acid polymers, the rate of strontium and calcium release as a function of pH and ionic strength of the vehicle can be adjusted to achieve release over an extended period of time.

Alginic acid and its salts are widely used in foods, cosmetics and in medical devices. The FDA has declared alginic acid GRAS (Generally Recognized as Safe). A similar safety classification exists in the European Union and other countries.

b. Polyvinylpyrrolidone (PVP)

Polyvinylpyrrolidone (PVP) is commonly used as an inert carrier of therapeutically active molecules. Due to the varying polar structure of the PVP polymer, it presents multiple, repeating sites to which atoms and molecules may bind via ionic forces. Upon subsequent exposure to ionic media, such as water, the bound substance may be released into the media over an extended period of time. Thus facilitating gradual release of the substance as a function of pH and other adjustable conditions, such as temperature, etc. As such, the PVP acts as a "molecular reservoir" providing for sustained release of therapeutic substances. The PVP polymer may be in its native form, or it may be chemically modified by derivatization and/or crosslinking to adjust the "releasing" properties of the polymer. In one embodiment, PVP is used as a carrier for gallic acid, related gallic acid-containing molecules or other polyhydroxyphenolic molecules.

PVP is used in foods, cosmetics and in medical devices. It is used as an excipient in FDA approved oral prescription drugs as a tablet binder.

In one embodiment, the compositions of the present disclosure include a strontium complex and a polymer capable of ionic association with the complex, in which case the complex and the polymer form a matrix. Such matrix formation enhances the bioavailability of the complexes and therefore prolongs the therapeutic effect of such complexes. In particular, when the strontium complex includes a polyhydroxyphenol, such compounds have a high affinity for polymers, such as polyvinylpyrrolidone (PVP).

For example, PVP is commonly used as an inert carrier of therapeutically active molecules. Due to the varying polar structure of the PVP polymer, it presents multiple, repeating sites to which atoms and molecules may bind via ionic forces. Upon subsequent exposure to ionic media, such as water, the bound substance may be released into the media over an extended period of time. Thus facilitating gradual release of the substance as a function of pH and other adjustable conditions, such as temperature, etc. As such, the PVP acts as a "molecular reservoir" providing for sustained release of therapeutic substances.

The PVP polymer may be in its native form, or it may be chemically modified by derivatization and/or crosslinking to adjust the "releasing" properties of the polymer.

The polyhydroxylated phenols, such as gallic acid, have a high affinity for PVP. As such, the combination of PVP, gallic acid and divalent cationic strontium forms a complex ionic matrix that facilitates controlled release of the strontium after administration.

Such polymer-based compositions also minimize osmolarity which can lead to unstable formulations and physically damage tissues and cause pain. For example, topical formulations with high osmotic activity may damage delicate tissues, especially in non-keratinized skin that has a mucous membrane or a damaged "barrier function" due to physical trauma, infection or inflammation.

c. Polyethylene Glycol (PEG)

Polyethylene glycol, polyethylene oxide, and polyethylene are polymers of ethylene oxide. As used herein, "PEG" will refer to all polymers of ethylene oxide. The molecular weight of PEG ranges from 300 g/mol to 10,000,000 g/mol. Additionally PEG can have several different geometries, such as linear, branched, star, and comb. The chain lengths and geometries can affect the physical properties of PEG.

16. Skin Penetration Enhancers

Experiments indicate that simple solutions of strontium and water can be effective at reducing pain and irritation when topically applied to skin. This indicates that strontium is able to pass through the outer layers of the skin without the inclusion of skin penetration enhancers. Without wishing to be bound by any one theory, it is believed that one way in which strontium passes through the outer layers of the skin is through the use of pilosebaceous unit. The pilosebaceous unit made up of a hair follicle, hair shaft, and sebaceous gland. The follicle is about 1-4 micrometers in diameter. The epidermis involutes to form the interior of the follicle. However, the tough outer most layer of the epidermis, i.e. the stratum corneum is much thinner and/or non-existent within the follicle. Accordingly, compounds that are small enough to pass through the hair follicle can penetrate through the skin better than larger compounds. The ability of strontium to penetrate the skin through the use of the hair follicle reduces the need to add skin penetration enhancers to the formulation. While skin penetration enhancers are not necessary, in some cases, in certain embodiments it is beneficial to include a skin penetration enhancer to formulations of the present disclosure. Non-limiting examples of skin penetration enhancers include lactic acid, sulfoxides, dimethylsulfoxide, azone and derivatives, pyrrolidones, fatty acids, essential oils, terpenes, terpenoids, oxazolidinones, urea and derivatives, alcohols, glycols, enzymes, surfactants, monooleins, iminosulfuranes, phospholipids, etc.

17. Extended Release Agents

Also contemplated are various chemicals that may prolong release of strontium or strontium and beneficial agent combinations. Such agents include, but are not limited to, polymers, liposome, microparticles, nanoparticles, film forming, and the like.

18. Other Pharmaceutical Excipients

The compounds of the present disclose may also be formulated with additional ingredients known in the pharmaceutical art to increase stability, increase disintegration of solid tablets, or increase customer appeal. Non-limiting examples possible excipients include preservatives, binders, bulking agents, diluents, sweeteners, flavorants, lubricants, and colorants.

Formulation and Administration

It is generally desirable to administer the compositions of the embodiments in a topical form; however, other routes of administration are also contemplated. Contemplated routes of administration include but are not limited to oral, parenteral, and subcutaneous. The compositions can be formulated into liquid preparations for, e.g., oral administration, when the tissue to be so treated comprises a membrane of the oral or gastrointestinal tract. Suitable such forms include suspensions, syrups, elixirs, and the like. Unit dosage forms configured for a single administration can be prepared; however, in certain embodiments it can be desirable to configure form for administration twice a day, or more.

In one embodiment, the compositions and formulations described herein can be formulated for topical application to epithelial cells/tissues including but not limited to keratinized cells/tissues, gastrointestinal tract, respiratory tract, reproductive tract, eyes, and ears. Non-limiting examples for application to keratinized tissues include powders, drops, vapors, mists, sprays, dressings, films, foams, gels, emulsions, lotions, creams, ointments, pastes, and solids. Non-limiting examples for application to the gastrointestinal tract include liquids, sprays, gels, powders, suppositories, and tablets. Non-limiting examples for application to the upper and lower respiratory tract include aerosols, powders, gels, and sprays. Non-limiting examples for application to the reproductive tract include sprays, gels, suppositories, tablets, creams, ointments, and foams. Non-limiting examples for application to the eyes and ears include drops, sprays, creams, and ointments.

Viscosity of the topical compositions can be maintained at the selected level using a pharmaceutically acceptable thickening agent. Methylcellulose can be employed as a readily and economically available excipient. Other suitable thickening agents include, for example, xanthan gum, carboxymethyl cellulose, hydroxypropyl cellulose, carbomer, and the like. The concentration of the thickener will depend upon the thickening agent selected. An amount is typically used that will achieve the selected viscosity. Viscous compositions are normally prepared from solutions by the addition of such thickening agents. In certain embodiments, no thickening agent is employed.

For oral administration, the pharmaceutical compositions can be provided as a tablet, aqueous or oil suspension, dispersible powder or granule, emulsion, hard or soft capsule, syrup or elixir. Compositions intended for oral use can be prepared according to any method known in the art for the manufacture of pharmaceutical compositions and can include one or more of the following agents: sweeteners, flavoring agents, coloring agents and preservatives. Aqueous suspensions can contain the active ingredient in admixture with excipients suitable for the manufacture of aqueous suspensions.

When administered orally in liquid form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or *arachis* oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

Formulations for oral use can also be provided as hard gelatin capsules, wherein the active ingredient(s) are mixed with an inert solid diluent, such as calcium carbonate, calcium phosphate, or kaolin, or as soft gelatin capsules. In soft capsules, the active compounds can be dissolved or suspended in suitable liquids, such as water or an oil medium, such as peanut oil, olive oil, fatty oils, liquid paraffin, or liquid polyethylene glycols. Stabilizers and microspheres formulated for oral administration can also be used. Capsules can include push-fit capsules made of gelatin, as well as soft, sealed capsules made of gelatin and a plasticizer, such as glycerol or sorbitol. The push-fit capsules can contain the active ingredient in admixture with fillers such as lactose, binders such as starches, and/or lubricants such as talc or magnesium stearate and, optionally, stabilizers. In instances where it is desirable to maintain components of the compositions in a reduced form, it can be desirable to include a reducing agent in the capsule or other dosage form.

Tablets can be uncoated or coated by known methods to delay disintegration and absorption in the gastrointestinal tract and thereby provide a sustained action over a longer period of time. For example, a time delay material such as glyceryl monostearate can be used. When administered in solid form, such as tablet form, the solid form typically comprises from about 0.001 wt. % or less to about 50 wt. % or more of active ingredient(s), preferably from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Tablets can contain the active ingredients in admixture with non-toxic pharmaceutically acceptable excipients including inert materials. For example, a tablet can be prepared by compression or molding, optionally, with one or more additional ingredients. Compressed tablets can be prepared by compressing in a suitable machine the active ingredients in a free-flowing form such as powder or granules, optionally mixed with a binder, lubricant, inert diluent, surface active or dispersing agent. Molded tablets can be made by molding, in a suitable machine, a mixture of the powdered compound moistened with an inert liquid diluent.

Preferably, each tablet or capsule contains from about 10 mg or less to about 1,000 mg or more of a compound of various embodiments, more preferably from about 20, 30, 40, 50, 60, 70, 80, 90, or 100 mg to about 150, 200, 250, 300, 350, 400, 450, 500, 550, 600, 650, 700, 750, 800, or 900 mg. Most preferably, tablets or capsules are provided in a range of dosages to permit divided dosages to be administered. A dosage appropriate to the patient and the number of doses to be administered daily can thus be conveniently selected. In certain embodiments it can be desired to incorporate two or more of the therapeutic agents to be administered into a single tablet or other dosage form (e.g., in a combination therapy); however, in other embodiments it can be desired to provide the therapeutic agents in separate dosage forms.

Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents can be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, karaya or tragacanth, or alginic acid or salts thereof.

Binders can be used to form a hard tablet. Binders include materials from natural products such as acacia, tragacanth, starch and gelatin, methyl cellulose, ethyl cellulose, carboxymethyl cellulose, polyvinyl pyrrolidone, hydroxypropylmethyl cellulose, and the like.

Lubricants, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, can be included in tablet formulations.

Surfactants can also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

Controlled release formulations can be employed wherein the strontium, BHB, and/or therapeutic compounds are incorporated into an inert matrix that permits release by either diffusion or leaching mechanisms. Slowly degenerating matrices can also be incorporated into the formulation. Other delivery systems can include timed release, delayed release, or sustained release delivery systems.

Coatings can be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments can be added for identification or to characterize different combinations of active compound doses.

When a compound of various embodiments is administered by intravenous, parenteral, or other injection, it is preferably in the form of a pyrogen-free, parenterally acceptable aqueous solution or oleaginous suspension. Suspensions can be formulated according to methods well known in the art using suitable dispersing or wetting agents and suspending agents. The preparation of acceptable aqueous solutions with suitable pH, isotonicity, stability, and the like, is within the skill in the art. A pharmaceutical composition for injection can contain an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils can be employed conventionally as a solvent or suspending medium. For this purpose, any bland fixed oil can be employed including synthetic mono or diglycerides. In addition, fatty acids such as oleic acid can likewise be used in the formation of injectable preparations. The pharmaceutical compositions can also contain stabilizers, preservatives, buffers, antioxidants, or other additives known to those of skill in the art.

The duration of the injection can be adjusted depending upon various factors, and can comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

The compositions of various embodiments can, in certain instances, be formulated to be isotonic with a body fluid of the recipient. The isotonicity of the compositions can be attained using sodium tartrate, propylene glycol or other inorganic or organic solutes. Sodium chloride can be employed, as can buffering agents such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils The compositions can be in admixture with a suitable carrier, diluent, or excipient such as sterile water, physiological saline, glucose, or the like, and can contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; $18^{th}$ and $19^{th}$ editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of penetration, and rate of clearance, and are thus chosen according to the intended application, such that the characteristics of the carrier are tailored to the selected route of administration.

The compositions of various embodiments can additionally employ adjunct components conventionally found in pharmaceutical compositions in their art-established fashion and at their art-established levels. Thus, for example, the compositions can contain additional compatible pharmaceutically active materials for combination therapy (such as supplementary antimicrobials, astringents, local anesthetics, anti-inflammatory agents, reducing agents, and the like), or can contain materials useful in physically formulating various dosage forms of various embodiments, such as excipients, dyes, thickening agents, stabilizers, preservatives or antioxidants.

A. Osmolarity

Strontium's anti-irritant activity is due to the divalent strontium ion. Pure strontium is highly reactive with oxygen and water. Accordingly, formulations containing strontium use strontium salts as the source of strontium. Due to its dual positive charges, two anionic counterions are required to balance the electrostatic charge and thereby create a strontium salt. With most commercially available strontium salts, the negatively-charged counterions, such as nitrate (NO3-)

or chloride (Cl—) contribute to the ionic strength and osmolarity of the formulation, but not to the overall anti-irritant benefits. Furthermore, clinical studies have shown that higher strontium concentrations produce increased clinical benefits.

Consequently, it is medically and commercially advantageous to create commercially acceptable and stable formulations with high strontium concentrations.

While high concentration strontium formulations would be clinically beneficial, they may also cause osmotic shock resulting in tissue damage and pain, especially in non-keratinized epithelium such as mucous membranes or in keratinized epithelium that has reduced barrier capabilities due to physical trauma, infection, or inflammation.

Various methods can be used to reduce osmotic shock. For example, using strontium based salts where the counterions also have therapeutic benefits. This would reduce the number of solutes when compared to formulations using standard strontium salts. In one embodiment, a salt of strontium and a polyhydroxyphenol is use. In another embodiment, a salt of strontium and a cysteine base antioxidant is used. In another embodiment, a salt of strontium, a polyhydroxyphenol, and a cysteine based antioxidant is used. Using the aforementioned strontium based salts would decrease the total solutes compared to formulations that combined strontium nitrate or strontium chloride with the polyhydroxyphenol or cysteine based antioxidants.

Another method that has been discovered to reduce osmotic shock is to combine the strontium cation with a carrier that does not affect osmolarity. For example, using polymers capable of binding the strontium cations. Non-limiting examples of polymers include polyethylene glycol, polyvinyl pyrrolidone, polyvinyl alcohol, polyacrylic acid, polyacrylamide, N-(2-hydroxypropyl) methacrylamide, divinyl ether-maleic anhydride, polyoxazoline, polyphosphates, polyphosphazene, xanthan gum, pectins, chitosan derivatives, dextran, carrageenan, iota carrageenan, guar gum, cellulose ethers, hydroxypropylmethyl cellulose, hydroxypropyl cellulose, hydroxyethyl cellulose, sodium carboxy methyl cellulose, hyaluronic acid, starch, and starch based derivatives.

Osmolarity may impact many formulations such as lotions, creams, and hydrogels rely on a delicate balance of factors that produce stable emulsions or hydrogels. Formulations with high ionic strengths may prevent stable emulsion formation. For example, emulsions in which more than about 6-7% strontium nitrate or strontium chloride hexahydrate (equivalent to about 2% elemental strontium) are incorporated tend to be unstable and separate. Similarly, hydrogels containing more than about 12% to 13% (equivalent to about 4% elemental strontium) of these salts also tend to be unstable.

B. pH

The pH of most topically applied formulations tends to match the pH of the surface it will be applied to. For example, the pH of skin ranges from 4 to 7, accordingly, most skin formulations (e.g. lotions, soaps, shampoo, etc.) are formulated with a pH between 4 and 7. Contrary to convention, it has been surprisingly found that topical strontium based formulations work better at a pH that is lower than the pH of the skin. In one embodiment, the pH of a topical formulation of the present disclosure is less than 4, or less than 3. In another embodiment, the pH is from about 2 to about 3.

C. Extended Release

The strontium based compounds described herein can be formulated for extended release. It is believed that long term exposure to strontium or strontium and beneficial agent combinations are useful in treating certain conditions such as neuropathic pain, itch, or irritation. Extended release can be achieved in a variety of methods; non-limiting examples include microencapsulation, specialized polymers, films, nanoparticles, and the like.

D. Formulation Aids

The strontium based compounds described herein can be formulated in a variety of forms. The form, e.g. lotion, emulsion, hydrogel, tablet, inhalant, etc., will dictate the additional ingredients/materials needed to make the final product. Additionally, ingredients to improve commercial appeal may be included. Non limiting examples include thickeners, flavorings, perfumes, colorants, lubricants, solvents, emulsifying agents, wetting agents, and drying agents.

E. Preservatives

A pharmaceutically acceptable preservative can be employed to increase the shelf life of the compositions. Benzyl alcohol can be suitable, although a variety of preservatives including, for example, parabens, thimerosal, chlorobutanol, or benzalkonium chloride can also be employed. A suitable concentration of the preservative is typically from about 0.02% to about 2% based on the total weight of the composition, although larger or smaller amounts can be employed depending upon the agent selected. Reducing agents can be advantageously used to maintain acceptable shelf life of the formulations.

Kits

The compounds of various embodiments can be provided to an administering physician or other health care professional, or for self-administration by the patient, in the form of a kit. The kit is a package which houses a container which contains the compositions in suitable packaging, and instructions for administering the composition. The kit can optionally also contain one or more additional therapeutic agents. For example, a kit containing one or more topical compositions in combination with one or more additional anesthetic, antibacterial, and/or anti-inflammation agents can be provided. The kit can also contain separate doses for serial or sequential administration. The kit can optionally contain one or more diagnostic tools and instructions for use. The kit can contain suitable delivery devices, e.g., syringes, wipes, or the like, along with instructions for administering the compositions and any other agent. The kit can optionally contain instructions for storage, reconstitution (if applicable), and administration of any or all compositions included. The kits can include a plurality of containers reflecting the number of administrations to be given to a subject.

Applicator Devices

The strontium based compounds described herein can be applied using a variety of applicator devices. Non-limiting examples include wraps, bandages, films, patches, rollers, syringes, sprayers, droppers, nebulizer, misters, and inhalers.

Methods of Use/Treatment

The strontium based compositions described herein are used to treat pain, pruritus, inflammation, irritation due to a variety of factors and conditions (e.g. medical conditions). Non-limiting examples include allergies, insect bites (e.g. hymenoptera, fleas, bed bugs, spiders, ants, ticks, etc.), stinging critters (e.g. jellyfish, scorpions, caterpillars, etc.) delayed type hypersensitivity, hives, exposure to venom, poison ivy, atopic dermatitis, eczema, herpes, shingles, acne, psoriasis, rosacea, ichthyosis vulgaris, dermatomyositis, thermal burns, ionizing radiation, exposure to chemicals, trauma, surgery, nerve compression, back pain, amputation, trauma, oral or throat ulcers, post herpetic neuralgia, multiple sclerosis, Parkinson's disease, lupus, diabetes, diabetic neuropathy, rheumatoid arthritis, psoriatic arthritis, ankylosing spondylitis, idiopathic arthritis, bacterial infections, viral infections, and drug use.

The strontium based compounds described herein are designed to be topically applied. Topical application in its broadest sense means application to epithelial surfaces such as skin or mucous membranes, including eyes, mouth, throat, esophagus, gastrointestinal tract, respiratory tract, and genitourinary tract.

In one embodiment, the strontium based compounds described herein are designed to be applied post incident or upon development of the condition. For example, the strontium based compounds are applied after exposure to poison ivy, after receiving an insect bite, after development of sunburn, or after psoriatic plaque develops, etc. In another embodiment, the strontium based compounds are regularly applied in the initial onset of symptoms or during the early stages of a condition to reduce or minimize the symptoms or skin damage associated with a condition. For example, applying the strontium based compounds to a cold sore area when the skin begins to itch, early stage psoriatic plaque, immediately after burn, etc. In another embodiment, the strontium based compounds are applied in a preventative manner to reduce of minimize the symptoms or skin damage that normally occurs with a given condition. For example, applying the strontium based compounds to the shingles rash area before the development of the rash, etc. In another embodiment, the strontium based compounds are applied on a regular basis as part of a normal daily routine. For example using a strontium+sunscreen or strontium+insect repellent or strontium+moisturizer composition as part of a normal daily routine. In another embodiment, the strontium based compounds are continuously applied to an affected area using extended release technology to desensitize hypersensitive or overactive nerves.

In another embodiment, the strontium based compounds described herein are designed to be used immediately after a traumatic event that is known to result in neuropathic condition. Non-limiting examples of traumatic events include surgical incisions, amputation, burns, compound or open bone fractures, and shingles. In many of these situations (e.g. burns, surgery), controlling infection is crucial to patient recovery. For those situations, the strontium based formulations usually include an antibacterial or antimicrobial such as iodine or silver.

Acute Conditions

In one embodiment, the strontium based compounds described herein are used to treat acute pain, pruritus, inflammation, or irritation. Acute pain, inflammation, or irritation generally lasts less than a month, or even less than two weeks, or even less than a week. Non-limiting examples of acute conditions include allergies, atopic dermatitis, eczema, stinging critters, insect bites, delayed type hypersensitivity, hives, exposure to venom, poison ivy, herpes, shingles, acne psoriasis, rosacea, thermal burns, back pain, ionizing radiation, exposure to chemicals, trauma, surgery, nerve compression, amputation, bacterial infection, and viral infection.

Chronic Conditions

In another embodiment, the strontium based compounds described herein are used to treat chronic pain, pruritus inflammation, or irritation. Chronic pain, inflammation, or irritation generally lasts longer than two weeks, or even longer than a month, or even longer than 3 months, or even longer than 6 months, or even longer than 9 months, or even longer than a year. Non-limiting chronic conditions include trauma, surgery, eczema, atopic dermatitis, psoriasis, rosacea, back pain, amputation, nerve compression, post herpetic neuralgia, multiple sclerosis, Parkinson's disease, lupus, diabetes, diabetic neuropathy, rheumatoid arthritis, psoriatic arthritis, and drug use.

A. Neuropathic Conditions

In another embodiment, the strontium based compounds described herein are used to treat neuropathic pain, pruritus, inflammation, or irritation. Neuropathic pain, pruritus, inflammation, or irritation can be either acute or chronic. Non-limiting examples of acute neuropathic conditions include trauma, surgical incisions, shingles, amputations, post herpetic neuralgia, and deep tissue burns (radiation or thermal). Non-limiting examples of chronic neuropathic conditions include nerve compression, post herpetic neuralgia, amputation, trauma, diabetic neuropathy, and drug use.

The strontium based compositions described herein are also used to prevent or reverse neuropathic conditions. Non-limiting examples of neuropathic conditions include nerve compression, nerve over sensitization, amputation/stump pain, post herpetic neuralgia, shingles, diabetic neuropathy, arthritis, bacterial infections, viral infections, and drug use.

In some embodiments, neuropathic conditions are treated using an extended release strontium based formulation. In other embodiments, acute neuropathic conditions are treated immediately after the neuropathic condition begins or occurs.

B. Preventing Development of Neuropathic Conditions

In another embodiment, the strontium based compounds described herein are used to prevent the development of neuropathic conditions as well as treat pain and itch. In situations where an event occurs that is known to cause neuropathic pain or itch, the early use of the compounds described herein may reduce or prevent the development of neuropathic pain or itch. Non-limiting examples of the event include trauma, burns, surgery, amputation, and shingles/zoster.

C. Preventing and/or Repairing Damaged Epithelial Tissue

The strontium based compounds described herein are also used to promote healing in damaged epithelial cells/tissue. Non-limiting examples include skin plaques, dermatoses, scale, ulcers, rashes, burns (heat, radiation, ionizing, etc.), acne, cold sores, hives, canker sores, blisters, shingles, warts, and boils. The above conditions may be due to a variety of causes such as (but not limited to) psoriasis, atopic dermatitis, bacteria, viruses, delayed type hypersensitivity, sun damage, excessive heat, radiation therapy, and allergies.

The strontium based compounds described herein are also use to prevent or reduce damage to epithelial tissue. Non-limiting examples include rashes, blisters, warts, burns (heat, radiation, ionizing, etc.), and hives. Non-limiting examples of causes include herpes, viruses, burns, sun damage, excessive heat, radiation therapy, exposure to allergens, insect bites, and stinging critters.

D. Joint Pain

The strontium based compounds described herein can also be used to treat joint pain. The joint pain can be in the neck, back, knee, ankle, toes, shoulder, elbow, wrist, or fingers. Non-limiting examples of causes of the joint pain include injury, arthritis, and repetitive motion.

E. Specific Conditions

In one embodiment, the strontium based compounds described herein are used to treat the pain, pruritus, inflammation, and irritation associated with herpes simplex infections. In another embodiment, the strontium based compounds described herein are used to reduce the intensity and duration of a herpes simplex infection.

In another embodiment, the strontium based compounds described herein are used to treat pain, pruritus, inflammation, and irritation associated with post herpetic neuralgia.

In another embodiment, the strontium based compounds described herein are used to treat pain, pruritus, inflammation, and irritation associated with diabetic neuropathy.

In another embodiment, the strontium based compounds described herein are used to treat pain, pruritus, inflammation, and irritation associated with radiation dermatitis.

In another embodiment, the strontium based compounds described herein are used to pain, pruritus, inflammation, and irritation associated with treat atopic dermatitis. In another embodiment, the strontium based compounds described herein are used to treat atopic dermatitis by breaking the inflammation/itch cycle.

In another embodiment, the strontium based compounds described herein are used to treat pain, pruritus, inflammation, and irritation associated with psoriasis. In another embodiment, the strontium based compounds described herein are used to treat psoriasis by breaking the inflammation/keratinocyte cycle.

In another embodiment, the strontium based compounds described herein are used to treat pain, pruritus, inflammation, and irritation associated with restless leg syndrome. In another embodiment, the strontium based compounds described herein are used to treat restless leg syndrome.

In another embodiment, the strontium based compounds described herein are used to treat pain, pruritus, inflammation, and irritation associated with joint pain. In another embodiment, the strontium based compounds described herein are used to treat joint pain.

EXAMPLES

Exemplary Formulation

Strontium and BHB are combined. Additionally, excipients are added to make a topical formulation.

Exemplary Formulation

Strontium, BHB, and colloidal oatmeal are combined. Additionally, excipients are added to make a topical formulation.

Exemplary Formulation

Strontium, BHB, and acetylcystine are combined. Additionally, excipients are added to make a topical formulation.

Exemplary Formulation

Strontium, BHB, and cystine are combined. Additionally, excipients are added to make a topical formulation.

Exemplary Formulation

Strontium and iodine are combined. Additionally, excipients are added to make a topical formulation.

Exemplary Formulation

Strontium, BHB, and iodine are combined. Additionally, excipients are added to make a topical formulation.

Exemplary Formulation

Strontium and silver are combined. Additionally, excipients are added to make a topical formulation.

Exemplary Formulation

Strontium, BHB, and silver are combined. Additionally, excipients are added to make a topical formulation.

Exemplary Formulation

Strontium, silver, and iodine are combined. Additionally, excipients are added to make a topical formulation.

Exemplary Formulation

Strontium, BHB, silver, and iodine are combined. Additionally, excipients are added to make a topical formulation.

Exemplary Synthesis

Synthesis of Thioester Bonded Beta-Hydroxybutyric Acid and NAC

Synthesis 1: The hydroxyl group of beta-hydroxybutyric acid was selectively protected as tert-butyl dimethyl silyl ether (TBS) using tert-butyl dimethyl silyl chloride and triethylamine in acetonitrile at 40-50° C. The solvent was partially removed and the hydroxy protected compound (Compound A) was precipitated with water. The product was washed with water and dried under vacuum.

Synthesis 2: Compound A was treated with N-hydroxysuccinimide in the presence of 1-ethyl-3-(3-dimethylaminopropyl) carbodimide (EDC) in acetonitrile to prepare the activated ester of the TBS protected beta-hydroxybutyric acid. The product was isolated and dried under vacuum (Compound B).

Synthesis 3: Compound B (NHS ester of the TBS protected beta-hydroxybutyric acid) was treated with N-acetyl cysteine in 1,4-dioxane/water mixture. The product was extracted with ethyl acetate and washed with water and brine (Compound C). The crude product precipitated from ethyl acetate/hexanes and dried under vacuum.

Synthesis 4: Compound C (TBS protected BHB:NAC) was dissolved in dichloromethane and treated with TFA to remove the TBS group. The reaction mixture was concentrated to dryness and washed with tert-butyl methyl ether (Compound D).

Synthesis 5: Compound D (BHB:NAC thioester) was treated with strontium acetate in water and the resulting strontium salt was precipitated by trituration of the mixture with acetone.

The final compound, strontium tripartite with thioester bond (Sr:BHB:NAC), was isolated and vacuum dried to yield a white crystalline solid (92%).

Exemplary Reaction

Cleaving of Thioester Bond Using Human Enzymes

The strontium tripartite with thioester bond compound synthesized as described above was subjected to enzymatic cleavage with three different enzymes, human carboxylesterase I (CES1), human carboxylesterase II (CES2), and S9 liver microsomes enzyme.

For each of the three enzymes evaluated, Sr:BHB:NAC was added to four sample tubes, A, B, C, and D. Enzyme was added to tubes A and B and 3-hydroxybutanoic acid was added to tube D. The samples were tested by monitoring the UV counts at time points 5, 60, 180, 360, 540, 1380 minutes by HPLC using a C18 column.

The results demonstrated that all three enzymes cleaved the thioester bond to release NAC and beta hydroxybutyrate.

Clinical Observation

BHB acts on the same pathway that causes flushing in individuals who take high doses of niacin. A topical formulation containing BHB was evaluated to see if it induced itching and erythema. The BHB formulation was compared to a topical niacin formulation.

A 1% BHB in water solution was made and a 1% niacin in water solution was made. Unknown to the subject, the BHB formula was applied in a 4×2 inch patch on the inside left forearm and the niacin formula was applied in a 4×2 in patch on the inside right forearm. The skin was evaluated over a period of time. Within minutes the right forearm where the niacin was applied began to redden and itch. Throughout the entire evaluation period, the left forearm with the BHB did not redden or become itchy.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless the context indicates otherwise. Similarly, a group of items linked with the conjunction 'or' should not be read as requiring mutual exclusivity among that group, but rather should be read as 'and/or' unless the context indicates otherwise.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B" unless the context indicates otherwise.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of actively or prophylactically treating inflammation or irritation associated with a condition selected from the group consisting of allergies, insect bites, stinging critters, delayed type hypersensitivity, hives, exposure to venom, poison ivy, atopic dermatitis, eczema, herpes, shingles, acne, psoriasis, rosacea, ichthyosis, vulgaris, dermatomyositis, thermal burns, ionizing radiation, exposure to chemicals, trauma, surgery, nerve compression, back pain, amputation, trauma, oral or throat ulcers, post herpetic neuralgia, multiple sclerosis, Parkinson's disease, lupus, diabetes, diabetic neuropathy, rheumatoid arthritis, psoriatic arthritis, ankylosing spondylitis, idiopathic arthritis, bacterial infections, viral infections, and drug use, the method comprising:
topically administering a composition comprising a complex of:
a divalent cationic strontium component;
a cysteine-based anti-oxidant selected from the group consisting of cystine, N-acetyl cysteine, N-acetyl cysteinate, N-acetyl cystine, N,S-diacetylcysteine, and esters thereof; and
a beta hydroxybutyrate;
wherein the cysteine-based anti-oxidant and the beta hydroxybutyrate are conjugated together by a cleavable bond,
to a patient in need thereof.

2. The method of claim 1, wherein the cysteine-based anti-oxidant is N-acetyl cysteine or an ester thereof.

3. The method of claim 1, wherein the divalent cationic strontium component is a strontium salt selected from the group consisting of strontium chloride, strontium chloride hexahydrate, strontium sulfate, strontium carbonate, strontium nitrate, strontium hydroxide, strontium hydrosulfide, strontium oxide, strontium acetate, strontium glutamate, strontium aspartate, strontium malonate, strontium maleate, strontium citrate, strontium threonate, strontium lactate, strontium pyruvate, strontium ascorbate, strontium alpha-ketoglutarate, and strontium succinate.

4. The method of claim 1, wherein the cleavable bond is selected from the group consisting of a peptide bond, an ester bond, a thioester bond, an enzymatically cleavable bond, a disulfide bond, and a pH dependent bond.

5. The method of claim 1, wherein the cleavable bond is a thioester bond.

6. The method of claim 1, comprising a complex of divalent cationic strontium, N-acetylcysteine or an ester thereof and beta hydroxybutyrate, wherein the N-acetylcysteine or an ester thereof and the beta hydroxybutyrate are conjugated together by a thioester bond formed by a sulfhydryl group of the N-acetylcysteine or an ester thereof and a carboxyl group of the beta hydroxybutyrate.

7. The method of claim 1, wherein the composition further comprises a polymer.

8. The method of claim 7, wherein the polymer is selected from the group consisting of polyvinylpyrrolidone, cyclodextrins, carrageenan, alginic acid, xanthan gum, sulfated polysaccharides, pentosan polysulfate, chondroitin sulfate, dextran sulfate and heparin sulfate.

9. The method of claim 8, wherein the polyvinylpyrrolidone is chemically modified by derivatization and/or crosslinking.

10. The method of claim 1, wherein the composition further comprises at least one pharmaceutically acceptable beneficial agent.

11. The method of claim 10, wherein the at least one pharmaceutically acceptable beneficial agent is selected from the group consisting of aluminum acetate, aspartame, colloidal oatmeal, corticosteroid, coal tar, antidepressants, antihistamines, plant extracts, local anesthetics, vitamins, ceramides, and moisturizers, and combinations thereof.

12. The method of claim 11, wherein the moisturizers are selected from the group consisting of lipids, fats, oils, waxes, humectants, glycerol, honey, shea butter, lanolin, hyaluronic acid, silicone, allantoin, and dimethicone, and combinations thereof.

13. The method of claim 11, wherein the corticosteroid is selected from the group consisting of alclometasone dipropionate, amcinonide, betamethasone dipropionate, clobetasol propionate, desonide, desoximetasone, diflorasone diacetate, fluocinolone acetonide, fluocinonide, flurandrenolide, fluticasone propionate, halcinonide, halobetasol propionate, halometasone, hydrocortisone, hydrocortisone butyrate, hydrocortisone valerate, mometasone furoate, prednisone, and triamcinolone acetonide, and combinations thereof.

14. The method of claim 11, wherein the local anesthetics are selected from the group consisting of benzocaine, butamben, dibucaine, lidocaine, oxybuprocaine, pramoxine, proparacaine, proxymetacaine, and tetracaine, and combinations thereof.

15. The method of claim 11, wherein the antihistamines are selected from the group consisting of acrivastine, azelastine, bilastine, brompheniramine, buclizine, bromodiphenhydramine, carbinoxamine, cetirizine, chlorpromazine, cyclizine, chlorpheniramine, chlorodiphenhydramine, clemastine, cyproheptadine, desloratadine, dexbrompheniramine, dexchlorpheniramine, dimenhydrinate, dimetindene, diphenhydramine, doxylamine, ebastine, embramine, fexofenadine, hydroxyzine, levocetirizine, loratadine, meclozine, mirtazapine, olopatadine, orphenadrine, phenindamine, pheniramine, phenyltoloxamine, promethazine, pyrilamine, quetiapine, rupatadine, tripelennamine, triprolidine, cimetidine, famotidine, lafutidine, nizatidine, ranitidine, roxatidine, and tiotidine, and combinations thereof.

16. The method of claim 1, wherein the composition further comprises at least one aromatic acid selected from the group consisting of histidine, tyrosine, phenylalanine, and tryptophan.

17. The method of claim 16, wherein the at least one aromatic acid is an L-isomer.

18. The method of claim 1, wherein the composition is configured for topical administration as at least one of a powder, drops, vapors, mists, sprays, dressings, films, foams, gels, emulsions, lotions, creams, ointments, pastes, liquids, solids, suppositories tablets and aerosols.

19. The method of claim 1, wherein the composition is applied using an applicator device.

20. The method of claim 19, wherein the applicator device is selected from the group consisting of a wrap, a bandage, and a film.

* * * * *